United States Patent
Fung et al.

(10) Patent No.: US 10,537,288 B2
(45) Date of Patent: *Jan. 21, 2020

(54) SYSTEM AND METHOD FOR BIOLOGICAL SIGNAL PROCESSING WITH HIGHLY AUTO-CORRELATED CARRIER SEQUENCES

(71) Applicant: Honda Motor Co., Ltd., Tokyo (JP)

(72) Inventors: Kin C. Fung, Dublin, OH (US);
Timothy J. Dick, Dublin, OH (US);
Charles William Hall, Jr., Hilliard, OH (US)

(73) Assignee: Honda Motor Co., Ltd., Tokyo (JP)

( * ) Notice: Subject to any disclaimer, the term of this patent is extended or adjusted under 35 U.S.C. 154(b) by 283 days.

This patent is subject to a terminal disclaimer.

(21) Appl. No.: 15/617,732

(22) Filed: Jun. 8, 2017

(65) Prior Publication Data
US 2017/0265816 A1 Sep. 21, 2017

Related U.S. Application Data

(63) Continuation-in-part of application No. 14/961,277, filed on Dec. 7, 2015, which is a continuation-in-part
(Continued)

(51) Int. Cl.
*G01N 33/48* (2006.01)
*G01N 33/50* (2006.01)
(Continued)

(52) U.S. Cl.
CPC ........ *A61B 5/7203* (2013.01); *A61B 5/02416* (2013.01); *A61B 5/0507* (2013.01);
(Continued)

(58) Field of Classification Search
None
See application file for complete search history.

(56) References Cited

U.S. PATENT DOCUMENTS

| 4,653,498 A | 3/1987 | New, Jr. et al. |
| 5,154,680 A | 10/1992 | Drzewiecki et al. |

(Continued)

FOREIGN PATENT DOCUMENTS

| DE | 102005020847 | 11/2006 |
| DE | 102008042342 | 4/2010 |

(Continued)

OTHER PUBLICATIONS

Office Action of U.S. Appl. No. 14/961,277 dated Feb. 12, 2018, 73 pages.

(Continued)

*Primary Examiner* — Russell S Negin
(74) *Attorney, Agent, or Firm* — Rankin, Hill & Clark LLP

(57) ABSTRACT

A computer-implemented method including, transmitting a high-spectrum energy wave towards a subject from a first sensor and transmitting a low-spectrum energy wave towards the subject from a second sensor. In response, modulation with a carrier sequence code results in a modulated evoked biological signal. The carrier sequence code has an autocorrelation function. The method includes demodulating the modulated evoked biological signal by calculating a convolution of the modulated evoked biological signal with the carrier sequence code resulting in an evoked biological signal spectrum. The evoked biological signal spectrum has a peak to sideband ratio as a function of the carrier sequence code. The method includes calculating deviations between each element of the sampled evoked biological signal and the peak to sideband ratio and filtering noise artifacts from the sampled evoked biological signal based on the deviations.

20 Claims, 15 Drawing Sheets

Related U.S. Application Data of application No. 14/697,593, filed on Apr. 27, 2015, now Pat. No. 10,153,796, which is a continuation-in-part of application No. 13/858,038, filed on Apr. 6, 2013, now Pat. No. 9,272,689.

(51) Int. Cl.

| | | |
|---|---|---|
| *A61B 5/00* | (2006.01) | |
| *A61B 5/024* | (2006.01) | |
| *G06K 9/00* | (2006.01) | |
| *B60R 25/25* | (2013.01) | |
| *G08C 17/02* | (2006.01) | |
| *A61B 5/05* | (2006.01) | |
| *H04B 1/10* | (2006.01) | |
| *G08C 17/00* | (2006.01) | |
| *G16H 10/60* | (2018.01) | |
| *A61B 5/18* | (2006.01) | |

(52) U.S. Cl.
CPC .......... *A61B 5/7207* (2013.01); *A61B 5/7214* (2013.01); *A61B 5/7228* (2013.01); *B60R 25/25* (2013.01); *G06K 9/0053* (2013.01); *G06K 9/00536* (2013.01); *G08C 17/00* (2013.01); *G08C 17/02* (2013.01); *H04B 1/10* (2013.01); *A61B 5/0059* (2013.01); *A61B 5/18* (2013.01); *A61B 5/7225* (2013.01); *G06K 2009/00939* (2013.01); *G16H 10/60* (2018.01)

(56) References Cited

U.S. PATENT DOCUMENTS

| | | | |
|---|---|---|---|
| 5,173,661 A | 12/1992 | Knüttel et al. | |
| 5,369,601 A | 11/1994 | Tannenbaum | |
| 5,521,823 A | 5/1996 | Akita et al. | |
| 5,609,158 A * | 3/1997 | Chan | A61B 5/0464 |
| | | | 600/518 |
| 5,617,871 A | 4/1997 | Burrows | |
| 5,719,950 A | 2/1998 | Osten et al. | |
| 6,026,340 A | 2/2000 | Corrado et al. | |
| 6,198,996 B1 | 3/2001 | Berstis | |
| 6,271,745 B1 | 8/2001 | Anzai et al. | |
| 6,810,309 B2 | 10/2004 | Sadler et al. | |
| 6,993,378 B2 | 1/2006 | Wiederhold et al. | |
| 7,147,601 B2 | 12/2006 | Marks et al. | |
| 7,149,653 B2 | 12/2006 | Bihler et al. | |
| 7,330,570 B2 | 2/2008 | Sogo et al. | |
| 7,403,804 B2 | 7/2008 | Ridder et al. | |
| 7,689,271 B1 | 3/2010 | Sullivan | |
| 7,756,558 B2 | 7/2010 | Ridder et al. | |
| 7,800,592 B2 | 9/2010 | Kerr et al. | |
| 7,933,315 B2 | 4/2011 | Li et al. | |
| 7,946,483 B2 | 5/2011 | Millet et al. | |
| 7,948,361 B2 | 5/2011 | Bennett et al. | |
| 8,068,562 B1 | 11/2011 | Zhang et al. | |
| 8,706,204 B2 | 4/2014 | Seo et al. | |
| 8,764,676 B2 | 7/2014 | Prakash et al. | |
| 8,773,239 B2 | 7/2014 | Phillips et al. | |
| 8,886,294 B2 | 11/2014 | Lisogurski et al. | |
| 8,930,145 B2 | 1/2015 | Li et al. | |
| 9,149,231 B2 | 10/2015 | Fujita et al. | |
| 9,751,534 B2 | 9/2017 | Fung et al. | |
| 2002/0097145 A1 | 7/2002 | Tumey et al. | |
| 2002/0156364 A1 | 10/2002 | Madore | |
| 2002/0176511 A1 | 11/2002 | Fullerton et al. | |
| 2003/0212336 A1 | 11/2003 | Lee et al. | |
| 2004/0088095 A1 | 5/2004 | Eberle et al. | |
| 2005/0058456 A1 | 3/2005 | Yoo | |
| 2005/0155808 A1 | 7/2005 | Braeuchle et al. | |
| 2005/0156457 A1 | 7/2005 | Breed et al. | |
| 2005/0242808 A1 | 11/2005 | McKendry et al. | |
| 2006/0180764 A1 | 8/2006 | Yajima et al. | |
| 2006/0208169 A1 | 9/2006 | Breed et al. | |
| 2007/0159344 A1 | 7/2007 | Kisacanin | |
| 2007/0237218 A1 | 10/2007 | Walker | |
| 2008/0027337 A1 | 1/2008 | Dugan et al. | |
| 2008/0146892 A1 | 6/2008 | LeBoeuf et al. | |
| 2008/0312376 A1 | 12/2008 | Mas et al. | |
| 2009/0027261 A1 | 1/2009 | Martin et al. | |
| 2009/0046538 A1 | 2/2009 | Breed et al. | |
| 2009/0054751 A1 | 2/2009 | Babashan et al. | |
| 2009/0284361 A1 | 11/2009 | Boddie et al. | |
| 2010/0030043 A1 | 2/2010 | Kuhn | |
| 2010/0066137 A1 | 3/2010 | Sakai et al. | |
| 2010/0113950 A1 | 5/2010 | Lin et al. | |
| 2010/0155609 A1 | 6/2010 | Silva | |
| 2010/0160794 A1 | 6/2010 | Banet et al. | |
| 2010/0217102 A1 | 8/2010 | LeBoeuf et al. | |
| 2011/0009754 A1 | 1/2011 | Wenzel et al. | |
| 2011/0066007 A1 | 3/2011 | Banet et al. | |
| 2011/0066042 A1 | 3/2011 | Pandia et al. | |
| 2011/0314737 A1 | 12/2011 | Schindhelm et al. | |
| 2012/0290215 A1 | 11/2012 | Adler et al. | |
| 2013/0060480 A1 | 3/2013 | Korhonen et al. | |
| 2013/0172771 A1 | 7/2013 | Muhlsteff | |
| 2013/0179163 A1 | 7/2013 | Herbig et al. | |
| 2013/0183646 A1 | 7/2013 | Lusted et al. | |
| 2013/0204466 A1 | 8/2013 | Ricci | |
| 2013/0245886 A1 | 9/2013 | Fung et al. | |
| 2013/0261415 A1 | 10/2013 | Ashe et al. | |
| 2013/0296666 A1 | 11/2013 | Kumar et al. | |
| 2014/0039330 A1 | 2/2014 | Seo et al. | |
| 2014/0058217 A1 | 2/2014 | Giovangrandi | |
| 2014/0073963 A1 | 3/2014 | Engelbrecht et al. | |
| 2014/0093244 A1 | 4/2014 | Zheng et al. | |
| 2014/0121927 A1 | 5/2014 | Hanita | |
| 2014/0188770 A1 | 7/2014 | Agrafioti et al. | |
| 2014/0228649 A1 | 8/2014 | Rayner et al. | |
| 2014/0275854 A1 | 9/2014 | Venkatraman et al. | |
| 2014/0275886 A1 | 9/2014 | Teixeira | |
| 2014/0303899 A1 | 10/2014 | Fung et al. | |
| 2015/0148691 A1 | 5/2015 | Moyer et al. | |

FOREIGN PATENT DOCUMENTS

| | | |
|---|---|---|
| DE | 102012208644 | 5/2013 |
| DE | 102012020901 | 4/2014 |
| DE | 102013200777 | 7/2014 |
| DE | 102013010928 | 12/2014 |
| EP | 2591969 | 5/2013 |
| JP | 2012212362 | 11/2012 |
| JP | 2012533474 | 12/2012 |
| WO | 2011038803 | 4/2011 |
| WO | 2012115220 | 8/2012 |
| WO | 2013164724 | 11/2013 |
| WO | 2014128273 | 8/2014 |

OTHER PUBLICATIONS

Office Action of U.S. Appl. No. 14/697,593 dated Nov. 24, 2017, 60 pages.

Wu, H., Rubinstein, M., Shih, E., Guttag, J. & Durand, F., Freeman, W., "Eulerian Video Magnification for Revealing Subtle Changes in the World," ACM Transactions on Graphics 31, No. 4 (Jul. 1, 2012): pp. 1-8.

Search Report of DE Serial No. 10 2014 206 648.4 dated Nov. 26, 2014, 9 pages.

Search Report of DE Serial No. 10 2014 206 648.4 dated Nov. 26, 2014, 8 pages (English translation).

Internet Video: CEATEC new chip detects motion, heartbeats—Videos (news)—PC Advisor printed Jan. 17, 2012.

Kavsaoğlu et al: "A novel feature ranking algorithm for biometric recognition with PPG signals", Computers in Biology and Medicine vol. 49, 2014, pp. 1-14.

Murata et al.: "Noninvasive Biological Sensor System for Detection of Drunk Driving", IEEE Transactions on Information Technology in Biomedicine, vol. 15, No. 1, Jan. 2011.

TruTouch Technologies: "Technology Overview" pp. 1-4, printed Apr. 27, 2015.

(56) References Cited

OTHER PUBLICATIONS

Brown et al.: "Framework for Multivariate Selectivity Analysis, Part I: Theoretical and Practical Merits", Applied Spectroscopy, vol. 59, No. 6, 2005, pp. 787-803.
Ridder et al.: "Framework for Multivariate Selectivity Analysis, Part II: Experimental Applications", Applied Spectroscopy, vol. 59, No. 6, 2005, pp. 804-815.
Press Release: "Faurecia keeps travelers fit, healthier in a heartbeat with "Active Wellness" car seat", Apr. 20, 2015.
Press Release: "Hoana Partners with Automotive Seat Manufacturer Faurecia to Introduce "Active Wellness™" at Auto Shanghai 2015", Apr. 20, 2015.
YouTube Video Link: https://www.youtube.com/watch?feature=youtu.be&v=_1UBDFSzQ28&app=desktop, printed on Apr. 27, 2015.
Article: http://www.faurecia.cn/jian-kang-mai-bo-fo-ji-ya-active-wellness-zuo-yi-wei-jia-cheng-zhe-jian-kang-hu-hang, printed on Apr. 27, 2015.
TruTouch Technologies prototype, Driver Alcohol Detection System for Safety, www.DADSS.org, 1 page.
Office Action of U.S. Appl. No. 13/858,038 dated Jun. 26, 2015, 19 pages.
International Search Report and Written Opinion of PCT/US2015/037019 dated Nov. 2, 2015, 12 pages.
Office Action of U.S. Appl. No. 13/858,038 dated Oct. 15, 2015, 12 pages.
Gircys, R. et al., "Movement Artefact Resistant Photoplethysmographic Probe", Elektronika Ir Elektrotechnika, IISN 1392-1215, vol. 20, No. 3, 2014, 4 pages.
Kuboyama, Yuta, "Motion Artifact Cancellation for Wearable Photoplethysmographic Sensor", B.S. Electrical Engineering and Computer Science, MIT, 2009, 66 pages.
Moharir, P.S. et al., "Optical Barker Codes", Electronics Letters, published May 2, 1974, vol. 10, No. 9, Mar. 28, 1974, 2 pages.
Office Action of U.S. Appl. No. 14/851,753 dated Sep. 27, 2016, 95 pages.
Office Action of U.S. Appl. No. 14/851,753 dated Dec. 21, 2016, 12 pages.
German Search Report of DE 102016207052.5 dated Mar. 1, 2017, 9 pages.
Office Action of U.S. Appl. No. 14/851,753 dated Mar. 22, 2017, 14 pages.
Office Action of U.S. Appl. No. 15/235,808 dated May 16, 2018, 60 pages.
Office Action of U.S. Appl. No. 14/697,593 dated May 18, 2018, 21 pages.
Office Action of U.S. Appl. No. 14/961,277 dated Jun. 15, 2018, 8 pages.
Office Action of U.S. Appl. No. 15/656,595 dated Oct. 2, 2018, 143 pages.
Office Action of U.S. Appl. No. 15/720,489 dated Oct. 1, 2018, 146 pages.
Nobata et al., Study of the Personal Authentication Technique Using ECG Signal toward Driver Recognition, 2 pages.
Office Action of U.S. Appl. No. 16/221,800 dated Aug. 29, 2019, 31 pages.
Notice of Allowance of U.S. Appl. No. 14/961,277 dated Oct. 8, 2019, 8 pages.
Extended European Search Report of related application No. EP 15811941.2 dated Aug. 3, 2018, 7 pages.

* cited by examiner

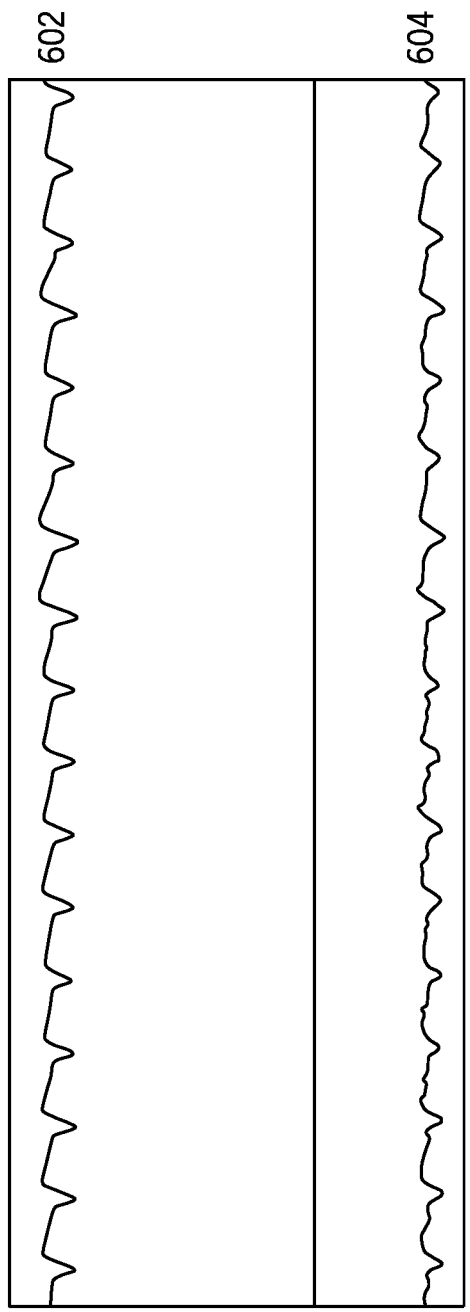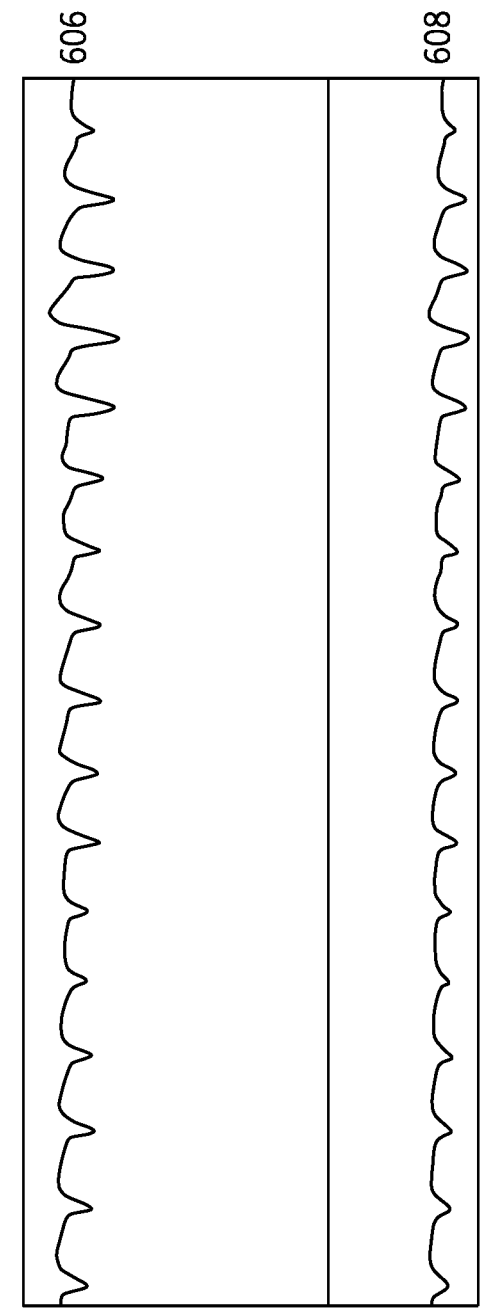

SYSTEM AND METHOD FOR BIOLOGICAL SIGNAL PROCESSING WITH HIGHLY AUTO-CORRELATED CARRIER SEQUENCES

RELATED APPLICATIONS

This application is a continuation-in-part of U.S. application Ser. No. 14/961,277 filed on Dec. 7, 2015 and now published as U.S. 2016/0157783, which is expressly incorporated herein by reference. U.S. application Ser. No. 14/961,277 is a continuation-in-part of U.S. application Ser. No. 14/697,593 filed on Apr. 27, 2015 and now published as U.S. 2015/0229341, which is expressly incorporated herein by reference. Further, U.S. application Ser. No. 14/697,593 is a continuation-in-part of U.S. application Ser. No. 13/858,038 filed on Apr. 6, 2013 and now issued as U.S. Pat. No. 9,272,689, which is also expressly incorporated herein by reference.

BACKGROUND

Biological signals are difficult to record when measured non-invasively from a body surface because the amplitude of the biological signals are low in relationship to the amplitude of ambient noise signals. Potential noise sources that can obscure measurement of biological signals from the body surface include broadcast electromagnetic radiation from electric or electronic devices, scattered electromagnetic radiation from neutral sources moving through static fields, mechanical vibrations in the environment transferring to the source and movement of the source itself, among others.

The impact of noise sources on biological signal recording can be minimized by electromechanically isolating a subject from potential interferences using electrical shielding and vibrational isolation. However, in real world applications, such control measures are not feasible and low signal recordings must be made in high noise environments. Further, the power spectrums of real world noise sources often overlap the power spectrums of the biological signal and as such are not amendable to conventional filtering techniques, such as bandpass filtering.

BRIEF DESCRIPTION

According to one aspect, a computer-implemented method includes transmitting a high-spectrum energy wave towards a subject from a first sensor according to a first control signal, and transmitting a low-spectrum energy wave towards the subject from a second sensor according to a second control signal. In response to transmitting the high-spectrum energy wave and transmitting the low-spectrum energy wave, the method includes receiving at a first receiver of the first sensor, an evoked biological signal from the subject, and receiving at a second receiver of the second sensor, an evoked noise signal from the subject. The method includes cancelling noise from the evoked biological signal based on the evoked noise signal, and calculating a sampled evoked biological signal by sampling the evoked biological signal at a predetermined sampling rate. Further, the method includes modulating the sampled evoked biological signal with a carrier sequence code resulting in a modulated evoked biological signal. The carrier sequence code has an autocorrelation function. Moreover, the method includes demodulating the modulated evoked biological signal by calculating a convolution of the modulated evoked biological signal with the carrier sequence code resulting in an evoked biological signal spectrum. The evoked biological signal spectrum has a peak to sideband ratio as a function of the carrier sequence code. Further, the method includes calculating deviations between each element of the sampled evoked biological signal and the peak to sideband ratio, filtering noise artifacts from the sampled evoked biological signal based on the deviations, and outputting a true evoked biological signal based on the filtering.

According to another aspect, a computer-implemented method includes transmitting a high-spectrum energy wave towards a subject from a first sensor according to a first control signal, and transmitting a low-spectrum energy wave towards the subject from a second sensor according to a second control signal. The first control signal represents a carrier sequence code. The method includes receiving at a first receiver of the first sensor an evoked biological signal in response to energy reflection returned from the subject. The evoked biological signal is an analog signal and modulated according to the carrier sequence code. The method includes receiving at a second receiver of the second sensor an evoked noise signal in response to energy reflection returned from the subject. Further, the method includes cancelling noise from the evoked biological signal based on the evoked noise signal and demodulating the evoked biological signal. The evoked biological signal is demodulated by calculating a convolution of the evoked biological signal with the carrier sequence code resulting in an evoked biological signal spectrum. The evoked biological signal spectrum has signal-to-noise ratio proportional to a peak to sideband ratio. The peak to sideband ratio is a function of the carrier sequence code. Further, the method includes generating a true evoked biological signal by extracting the true evoked biological signal from the evoked biological signal based on the peak to sideband ratio.

According a further aspect, a system includes a first sensor including a first transmitter to transmit first control signals to a first transmission source. The first transmission source transmits a high-spectrum energy wave towards a subject according to the first control signals. The first sensor also includes a first receiver to receive an evoked biological signal in response to energy reflection returned from the subject. The evoked biological signal is an analog signal. The system also includes a second sensor, communicatively coupled to the first sensor, the second sensor including a second transmitter to transmit second control signals to a second transmission source. The second transmission source transmits a low-spectrum energy wave towards the subject according to the second control signal. The second sensor further includes a second receiver to receive an evoked noise signal in response to energy reflection returned from the subject. The system also includes a filter, communicatively coupled to the first sensor and the second sensor. The filter cancels noise from the evoked biological signal based on the evoked noise signal. The system includes a system clock, communicatively coupled to the first sensor, the second sensor, and the filter. The system clock generates a sampled evoked biological signal at a predetermined sampling rate.

Further, the system includes a modulator, communicatively coupled to the first sensor, the second sensor, and the filter. The modulator receives the sampled evoked biological signal and modulate the sampled evoked biological signal with a carrier sequence code having an autocorrelation function. A demodulator, communicatively coupled to the first sensor, the second sensor, and the filter, receives the modulated evoked biological signal and demodulates the modulated evoked biological signal by calculating a convolution of the modulated evoked biological signal with the carrier sequence code resulting in an evoked biological signal spectrum. The evoked biological signal spectrum having a peak to sideband ratio as a function of the carrier sequence code. The filter calculates deviations between the sampled evoked biological signal and the peak to sideband ratio, filters noise artifacts from the sampled evoked biological signal based on the deviations, and outputs a true evoked biological signal based on the filtering.

According to a further aspect, a system includes a first sensor including a first transmitter to transmit first control signals according to a carrier sequence code to a first transmission source. The first transmission source transmits high-spectrum energy towards a subject according to the carrier sequence code. The carrier sequence code has an autocorrelation function. The first sensor further includes a first receiver to receive an evoked biological signal in response to energy reflection returned from the subject. The evoked biological signal is an analog signal and modulated according to the carrier sequence code. The system includes a second sensor including a second transmitter to transmit second control signals to a second transmission source. The second transmission source transmits low-spectrum energy towards the subject. The second sensor further includes a second receiver to receive an evoked noise signal in response to energy reflection returned from the subject. The system also includes a filter including an amplifier for cancelling noise from the evoked biological signal based on the evoked noise signal. The system also includes a demodulator to demodulate the evoked biological signal by calculating a convolution of the evoked biological signal with the carrier sequence code resulting in an evoked biological signal spectrum. The evoked biological signal spectrum has a signal-to-noise ratio proportional to a peak to sideband ratio. The peak to sideband ratio is a function of the carrier sequence code. The demodulator generates a true evoked biological signal by extracting the true evoked biological signal from the evoked biological signal based on the peak to sideband ratio.

BRIEF DESCRIPTION OF THE DRAWINGS

FIG. 6A illustrates an exemplary graphic output of measuring an evoked biological signal in a real world application without using HACS;

FIG. 6B illustrates an exemplary graphic output of measuring an evoked biological signal in a real world application using HACS and varying predetermined sampling rates.

DETAILED DESCRIPTION

Figure 1:
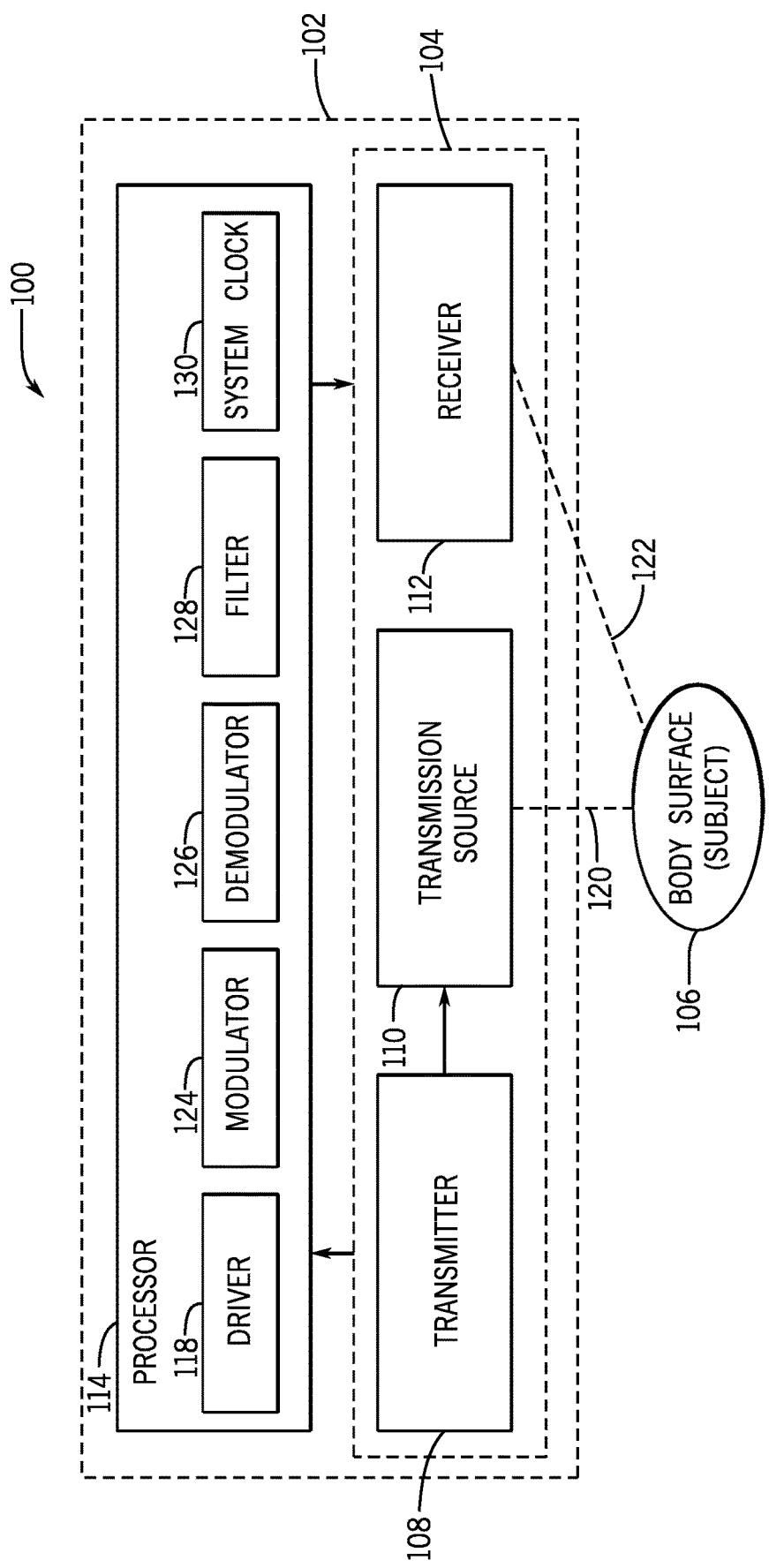
FIG. 1 is an exemplary block diagram of a system for biological signal processing using highly auto-correlated carrier sequence codes (HACS) according to an a exemplary embodiment.

The following includes definitions of selected terms employed herein. The definitions include various examples and/or forms of components that fall within the scope of a term and that can be used for implementation. The examples are not intended to be limiting. Further, the components discussed herein, can be combined, omitted or organized with other components or organized into different architectures.

"Computer communication", as used herein, refers to a communication between two or more computing devices (e.g., computer, personal digital assistant, cellular telephone, network device) and can be, for example, a network transfer, a file transfer, an applet transfer, an email, a hypertext transfer protocol (HTTP) transfer, and so on. A computer communication can occur across, for example, a wireless system (e.g., IEEE 802.11), an Ethernet system (e.g., IEEE 802.3), a token ring system (e.g., IEEE 802.5), a local area network (LAN), a wide area network (WAN), a point-to-point system, a circuit switching system, a packet switching system, among others.

"Computer-readable medium", as used herein, refers to a non-transitory medium that stores instructions and/or data. A computer-readable medium may take forms, including, but not limited to, non-volatile media, and volatile media. Nonvolatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

A "disk", as used herein can be, for example, a magnetic disk drive, a solid state disk drive, a floppy disk drive, a tape drive, a Zip drive, a flash memory card, and/or a memory stick. Furthermore, the disk can be a CD-ROM (compact disk ROM), a CD recordable drive (CD-R drive), a CD rewritable drive (CD-RW drive), and/or a digital video ROM drive (DVD ROM). The disk can store an operating system that controls or allocates resources of a computing device.

A "database", as used herein can refer to table, a set of tables, a set of data stores (e.g., disks) and/or methods for accessing and/or manipulating those data stores.

A "memory", as used herein can include volatile memory and/or nonvolatile memory. Non-volatile memory can include, for example, ROM (read only memory), PROM (programmable read only memory), EPROM (erasable PROM), and EEPROM (electrically erasable PROM). Volatile memory can include, for example, RAM (random access memory), synchronous RAM (SRAM), dynamic RAM (DRAM), synchronous DRAM (SDRAM), double data rate SDRAM (DDRSDRAM), and direct RAM bus RAM (DRRAM). The memory can store an operating system that controls or allocates resources of a computing device.

A "processor", as used herein, processes signals and performs general computing and arithmetic functions. Signals processed by the processor can include digital signals, data signals, computer instructions, processor instructions, messages, a bit, a bit stream, that can be received, transmitted and/or detected. Generally, the processor can be a variety of various processors including multiple single and multi-core processors and co-processors and other multiple single and multicore processor and co-processor architectures. The processor can include various modules to execute various functions.

A "vehicle," as used herein, refers to any moving vehicle that is capable of carrying one or more human occupants and is powered by any form of energy. The term "vehicle" includes, but is not limited to cars, trucks, vans, minivans, SUVs, motorcycles, scooters, boats, personal watercraft, and aircraft. In some cases, a motor vehicle includes one or more engines. Further, the term "vehicle" can refer to an electric vehicle (EV) that is capable of carrying one or more human occupants and is powered entirely or partially by one or more electric motors powered by an electric battery. The EV can include battery electric vehicles (BEV) and plug-in hybrid electric vehicles (PHEV). Additionally, the term "vehicle" can refer to an autonomous vehicle and/or self-driving vehicle powered by any form of energy. The autonomous vehicle may or may not carry one or more human occupants.

Referring now to the drawings, wherein the showings are for purposes of illustrating one or more exemplary embodiments and not for purposes of limiting same, FIG. 1 is a block diagram of a system 100 for biological signal recording using highly auto-correlated carrier sequence codes (HACS) according to an exemplary embodiment. The components FIG. 1, as well as the components of other systems, hardware architectures, and software architectures discussed herein, can be combined, omitted, or organized into different architectures for various embodiments. In some embodiments, the components of the system 100 can be implemented within a vehicle 102, for example, as discussed in U.S. application Ser. No. 14/697,593, now published as U.S. 2015/0229341, which is expressly incorporated herein by reference.

In FIG. 1, the system 100 includes a sensor 104 for measuring biological signals from a subject. In one embodiment, the sensor 104 is a sensor for detecting plethysmograph (PPG) measurements from a body surface of a subject 106. In particular, the sensor 104 can measure changes in transmission or diffused reflectance from the body surface (e.g., body tissue) of the subject 106 under active illumination. More specifically, the sensor 104 can include a transmitter 108, a transmission source 110, and a receiver 112. The sensor 104 can also include and/or be communicatively coupled to a processor 114. The processor 114 can include other components to facilitate biological signal recording as will be discussed in further detail herein.

It is understood that the system 100 can include more than one sensor 104. Further, as discussed above and detailed in U.S. application Ser. No. 14/697,593, in some embodiments, the sensor 104 can be located in a vehicle 102. For example, in some embodiments one or more sensors can be part of one or more sensor assemblies. Additionally, one or more sensors can be mechanically coupled to a vehicle seat of the vehicle 102. In other embodiments, the sensor 104 and/or the processor 114 could be integrated with a vehicle computing device, for example, a head unit (not shown).

Referring again to the sensor 104 of FIG. 1, the transmitter 108 controls the transmission source 110. More specifically, the transmitter 108 transmits control signals (not shown) to the transmission source 110 and the transmission source 110 transmits energy (e.g., a energy signal) towards the subject 106 according to the control signals. It is understood that the energy transmitted by the transmission source 110 can include, but is not limited to, light, ultrasound, sonic, and sound waves, magnetic resonance imaging using magnetic waves, electromagnetic waves, millimeter radar, computed tomography and X-ray devices using gamma rays, among others. For example, in one embodiment, which will be used as an illustrative example herein, the transmission source 110 can include at least one light source (e.g., light emitting diode (LED), laser, laser diode) that can transmit light of a particular wavelength.

In some embodiments, the processor 114 can include a driver 118 which controls the transmitter 108 and/or the transmission source 110. In other embodiments, the driver 118 can be a component of the sensor 104 and/or the transmitter 108. The transmitter 108 and/or the driver 118 can include driver circuitry and controllers to drive the control signals to the transmission source 110 to driver energy (e.g., transmit energy (e.g., energy waves) towards the subject 106) as desired. For example, the transmitter 108 and/or the driver 118 can cause the transmission source 110 to drive energy based on a pulsed basis or a continuous basis. In one embodiment, discussed herein, the illumination can be pulsed (e.g., blinked) according to a carrier sequence code with an autocorrelation function. In FIG. 1, the energy wave transmitted to the subject 106 is indicated by the dashed line 120.

Upon transmission of the energy wave 120 towards the subject 106, energy is reflected from the subject 106 and received by the receiver 112 to generate data signals therefrom. In FIG. 1, the reflected energy, which is an evoked biological signal, is indicated by the dashed line 122. The receiver 112 captures the reflected energy as an electrical signal in analog form. More specifically, the receiver 112 receives an evoked biological signal 122 representing a biological measurement (e.g., a PPG measurement) of the subject 106. As will be discussed herein, the receiver 112 can processes these analog signals and/or transmit the analog signals for processing to, for example, the processor 114.

With respect to the processor 114, the sensor 104 can include the processor 114 and/or the processor 114 can be included as part of another system communicatively coupled to the sensor 104. For example, the processor 114 can be part of a monitoring system (not shown) integrated with the vehicle 102. In addition to the driver 118, the processor 114 can also include a modulator 124, a demodulator 126, a filter 128, and a system clock 130. It is understood that the processor 114 can include other components not shown, for example, memory, a data store, communication interfaces, among others. It is also understood that some or all of the components of the processor 114 can be integrated with the sensor 104 and/or components of the sensor 104. It is further understood that the highly auto-correlated carrier sequence codes (HACS) used for modulation and demodulation discussed herein, can be stored at one or more of the components of the system 100.

As will be described in more detail herein, the modulator 124 facilitates modulation of the evoked biological signal 122. The demodulator 126 facilitates demodulation of the evoked biological signal 122. Further, the demodulator 126 and/or the filter 128 can generate a true biological signal from the evoked biological signal 122 free of noise artifacts that can contaminate the evoked biological signal 122. The system clock 130 controls sampling of the evoked biological signals at different sampling rates. Each of these components will be described in further detail herein.

Exemplary operation of the system 100 with reference to FIG. 1 according to an exemplary embodiment will now be described. As discussed above, in one embodiment, the system 100 includes the sensor 104 with the transmitter 108. The transmitter 108 transmits control signals to the transmission source 110. The transmission source transmits energy (i.e., energy wave 120) towards the subject 106 according to the control signals. Further, the sensor 104 includes the receiver 112 to receive an evoked biological signal 122 in response to energy reflection returned from the subject 106. The evoked biological signal 122 can be a data signal in electrical format. More specifically, the evoked biological signal 122 is an analog signal.

The evoked biological signal 122 can be contaminated by noise and motion artifacts from sources surrounding the sensor 104 and the subject 106. For example, in a vehicle setting, vibration from the vehicle 102 and other noises within and outside of the vehicle 102 can contaminate the evoked biological signal 122. In some instances, the frequencies and/or power spectrums of the noise and motion artifacts can overlap with the frequencies and/or power spectrums of the evoked biological signal 122. This overlap can cause issues in obtaining a true biological signal free of noise and motion artifacts.

Accordingly, in one embodiment, the system clock 130, which is communicatively coupled to the sensor 104, can generate a sampled evoked biological signal at a predetermined sampling rate. For example, the predetermined sampling rate can be 4 ms or less. The sampled evoked biological signal can be expressed in vector form as $A=(a_1, a_2, a_3, a_4, a_5, a_6, a_7 \ldots)$, where A represents the evoked biological signal 122 and each element in A represents $A(i_t)$, where t is the sampling rate and/or sampling interval. Modulation based on the sampled evoked biological signal can be configured to increase the amplitude of the evoked biological signal 122 in relation to noise and motion artifacts that can contaminate the evoked biological signal.

More specifically, the modulator 124, which is communicatively coupled to the sensor 104, can receive the sampled evoked biological signal and modulate the sampled evoked biological signal with a carrier sequence code having an auto correlation function. The carrier sequence code can be a highly auto-correlated carrier sequence (HACS) to process the evoked biological signal 122. Exemplary HACS include, but are not limited to, Barker codes, Frank codes, Golay codes, poly-time codes, among others. Barker codes will be used in exemplary embodiments disclosed herein, however the systems and methods discussed herein can be implemented with other types of HACS. Further, throughout the specification, a Barker code of length seven (7) will be discussed, however, it is understood that Barker codes and other carrier sequence codes of different lengths can be implemented. Furthermore, it is understood that Barker Codes and other HACS of varying lengths can be combined to produce HACS that can also be implemented in these methods and systems.

In one embodiment, the modulator 124 modulates the sampled evoked biological signal by multiplying the sampled evoked biological signal by the carrier sequence code. The number of samples in the sampled evoked biological signal is equal to the length of the carrier sequence code. As an illustrative example, seven (7) elements of the sampled evoked biological signal A, discussed above, can be multiplied with a Barker Code $B_7$ having a length of seven (7). Barker Code $B_7$ can be expressed as $B_7=(1, 1, 1, -1, -1, 1, -1)$. Accordingly, the sampled evoked biological signal multiplied by Barker Code $B_7$ results in modulation of the sampled evoked biological signal, which is expressed in vector format as $AB_7=(a_1, a_2, a_3, -a_4, -a_5, a_6, -a_7)$. Modulation of the sampled evoked biological signal can be calculated using bitwise shifting of each sampled point of the sampled evoked biological signal with the carrier sequence code. For example, $A=(a_1, a_2, a_3, a_4, a_5, a_6, a_7)$ can be multiplied by $B_7=(1, 1, 1, -1, -1, 1, -1)$ using bitwise multiplication shifting from the right.

Figure 2:
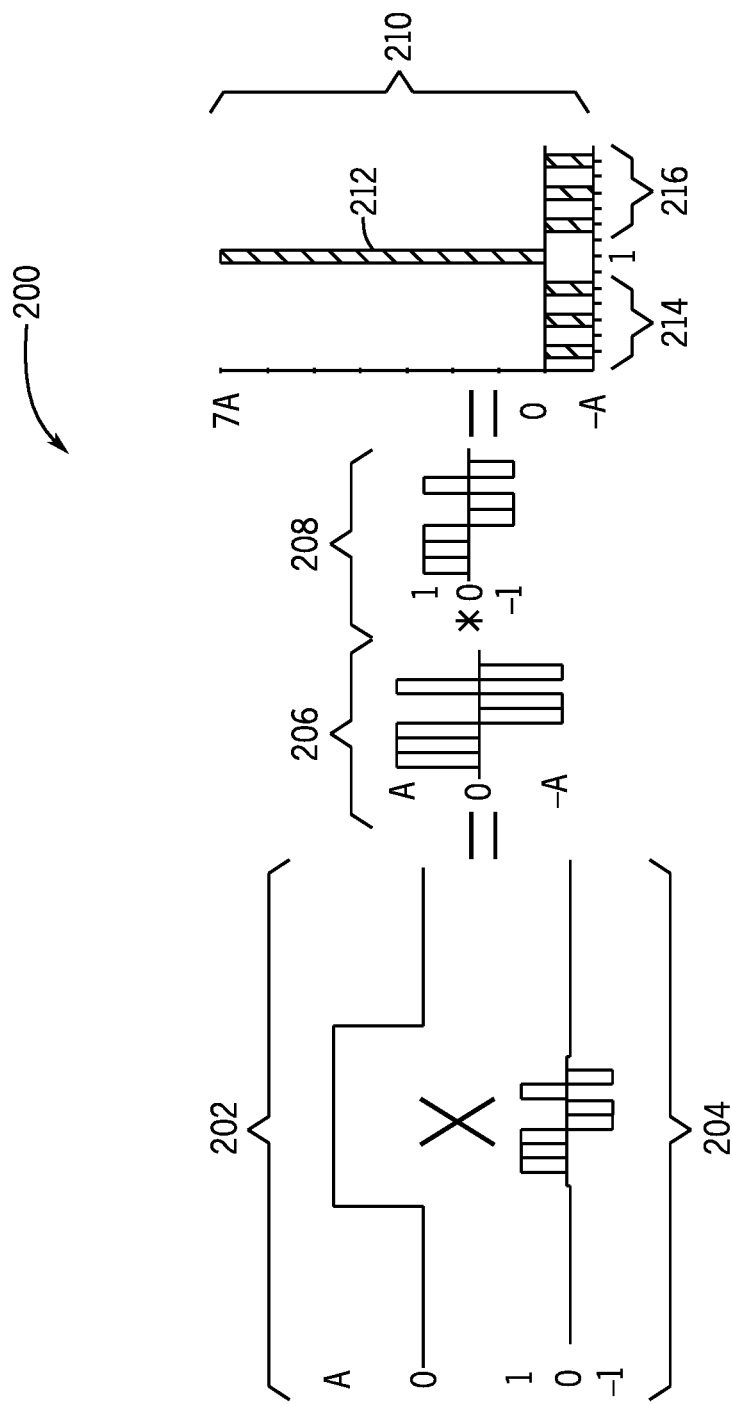
FIG. 2 is an exemplary schematic diagram of modulation and demodulation for biological signal processing using HACS according to an exemplary embodiment.

Referring now to FIG. 2, an exemplary schematic diagram of modulation and demodulation for biological signal recording using HACS according to an exemplary embodiment is shown. In this example, signal A 202 (i.e., the evoked biological signal 122) has an amplitude ½ of the noise N in the surrounding environment. Signal A 202 is modulated with the Barker Code $B_7$ 204. For example, signal A 202 is multiplied by Barker Code $B_7$ 204 resulting in a Barker segment $AB_7$ 206 (e.g., $AB_7=(a_1, a_2, a_3, -a_4, -a_5, a_6, -a_7)$). Thus, modulating the sampled evoked biological signal results in a modulated evoked biological signal with amplitude proportional to the carrier sequence code. More specifically, as shown in FIG. 2, the Barker segment $AB_7$ 206 has an amplitude ratio of +/−A.

Referring again to FIG. 1, to reconstruct a true biological signal free of noise and/or motion artifacts, the demodulator 126, which is communicatively coupled to the sensor 104, receives the modulated evoked biological signal, and demodulates the modulated evoked biological signal with the carrier sequence code. In one embodiment, the demodulator 126 calculates a convolution of the modulated evoked biological signal with the carrier sequence code. Referring again to the illustrative example discussed above and to FIG. 2, the modulated evoked biological signal is represented by Barker segment $AB_7$ 206 (i.e., $AB_7=(a_1, a_2, a_3, -a_4, -a_5, a_6,$ $-a_7$). The Barker segment $AB_7$ 206 is convolved with the original Barker Code $B_7$. This convolution results in an evoked biological signal spectrum. Thus, in FIG. 2, $AB_7$ 206 is convolved with Barker Code $B_7$ 208, which is the same as the original Barker code used for modulation, Barker Code $B_7$ 204. The resulting evoked biological signal spectrum is shown graphically as evoked biological signal spectrum 210.

As shown in FIG. 2, the evoked biological signal spectrum 210 has a peak to sideband ratio as a function of the carrier sequence code (i.e., in FIG. 2, the Barker Code $B_7$). Specifically, in FIG. 2, peak 212 has amplitude 7A and there are six (6) sidebands 214, 216 on each side of the peak 212. In this example, the signal to noise ratio of the demodulated evoked biological signal is 7A/N. As discussed above, in this example, the amplitude of signal A 204 is ½ the noise N in the environment. Thus, after demodulation, the new signal to noise ratio is 7/2=3.5.

The evoked biological signal spectrum 210 illustrated in FIG. 2 is shown quantitatively in Table 1. Table 1 represents the evoked biological signal spectrum 210 based on the convolution of $AB_7$ with $B_7$. Accordingly, as shown in Table 1, at step 7, the amplitude is 7A. A peak to sideband ratio can be determined by calculating the absolute value of the sum at step 7 (i.e., $a_1+a_2+a_3+a_4+a_5+a_6+a_7$) divided by the sums of at steps 1, 3, 5, 9, 11, and 13 (i.e., $a_1+a_3+a_5+a_9+a_{11}+a_{13}$). This results in a peak to sideband ratio equal to 7A/-6A=-7/6.

TABLE 1

| Step(i) | Measured $(AB_7 * B_7)_i$ | Theoretical $(AB_7 * B_7)_i$ |
| --- | --- | --- |
| $(AB_7 * B_7)_1$ | $-a_7$ | $-A$ |
| $(AB_7 * B_7)_2$ | $a_6 - a_7$ | 0 |
| $(AB_7 * B_7)_3$ | $-a_5 + a_6 - a_7$ | $-A$ |
| $(AB_7 * B_7)_4$ | $-a_4 - a_5 + a_6 + a_7$ | 0 |
| $(AB_7 * B_7)_5$ | $a_3 - a_4 - a_5 - a_6 + a_7$ | $-A$ |
| $(AB_7 * B_7)_6$ | $a_2 + a_3 - a_4 + a_5 - a_6 - a_7$ | 0 |
| $(AB_7 * B_7)_7$ | $a_1 + a_2 + a_3 + a_4 + a_5 + a_6 + a_7$ | 7A |
| $(AB_7 * B_7)_8$ | $a_1 + a_2 - a_3 + a_4 - a_5 - a_6$ | 0 |
| $(AB_7 * B_7)_9$ | $a_1 - a_2 - a_3 - a_4 + a_5$ | $-A$ |
| $(AB_7 * B_7)_{10}$ | $-a_1 - a_2 + a_3 + a_4$ | 0 |
| $(AB_7 * B_7)_{11}$ | $-a_1 + a_2 - a_3$ | $-A$ |
| $(AB_7 * B_7)_{12}$ | $a_1 - a_2$ | 0 |
| $(AB_7 * B_7)_{13}$ | $-a_1$ | $-A$ |

With respect to convolving the modulated evoked biological signal with the carrier sequence code, it is understood that the demodulator 126 can calculate the convolution using bitwise shifting with a logical AND gate. Further, in cases where the transmission source 110 is an LED or other pulsating device, the carrier sequence code can be converted to binary format. Specifically, the carrier sequence code can be modified to account for an ON (i.e., 1) or OFF (i.e., 0) status of the transmission source 110. Thus, in one embodiment, the modulator 124 can modulate the sampled evoked biological signal by converting the carrier sequence code to binary format and modulating the sampled evoked biological signal with the carrier sequence code in binary format. Referring again to the illustrative example, the carrier sequence code $B_7$=(1, 1, 1, -1, -1, 1, -1) can be converted to binary format as $B_{7d}$=(1,1,1,0,0,1,0). Thus, the modulator 124 can modulated the evoked biological signal by multiplying the sampled evoked biological signal by the modified carrier sequence code in binary format (i.e., $B_{7d}$=(1,1,1,0, 0,1,0)).

Figure 3A:
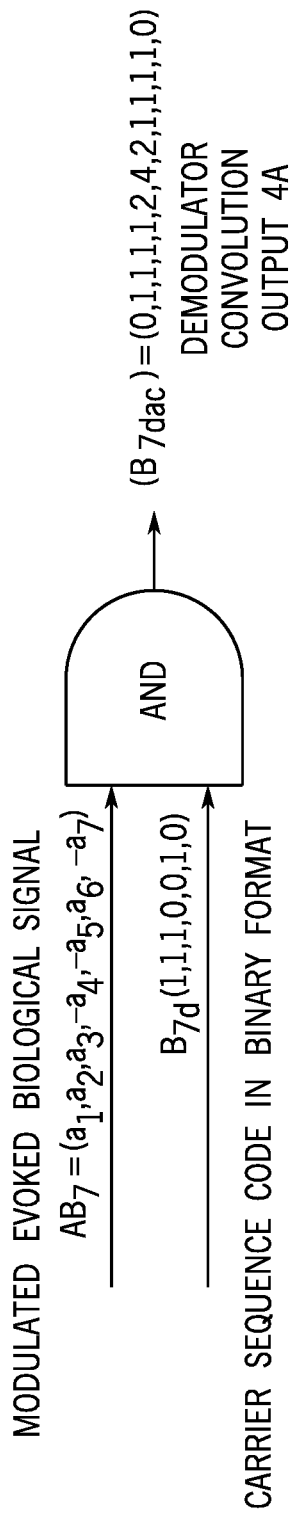
FIG. 3A is a schematic diagram of exemplary biological signal convolution using HACS and a logical AND gate according to an exemplary embodiment.

According to the embodiment discussed above, the demodulator 126 can demodulate the modulated evoked biological signal by calculating the convolution of the modulated evoked biological signal with the carrier sequence code in binary format, for example, using a logical AND gate. Referring again to the illustrative example, the demodulator can calculate the convolution of $B_{7d}$=(1,1,1,0, 0,1,0) with $AB_7$=($a_1$, $a_2$, $a_3$, $-a_4$, $-a_5$, $a_6$, $-a_7$) using a logical AND gate, the result of which is $(B_{7dac})$=(0,1,1,1,1,2,4,2,1, 1,1,1,1,0). In this example, the resulting evoked biological signal spectrum has an amplitude of 4A with peak adjacent sidebands of 2, and more distant sidebands of 1, and a peak to sideband ratio of 4/12. FIG. 3A of exemplary biological signal convolution using HACS and a logical AND gate according to the example described above.

Figure 3B:
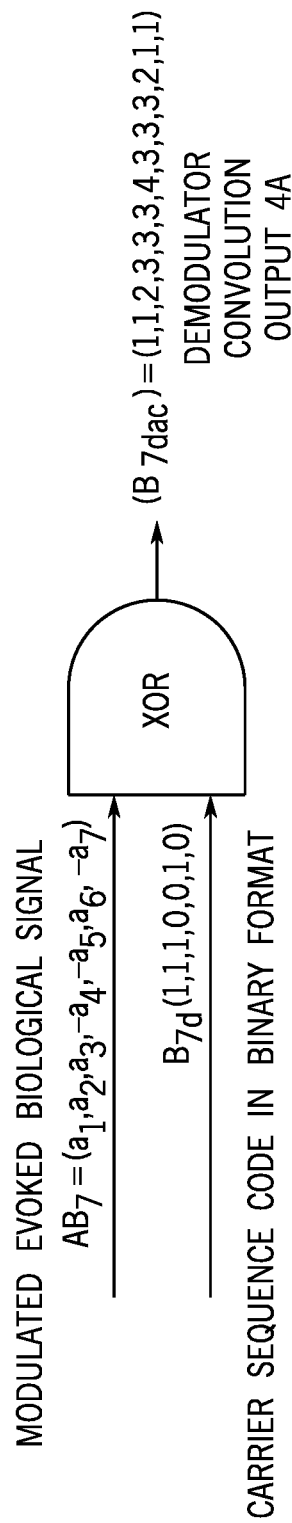
FIG. 3B is a schematic diagram of exemplary biological signal convolution using HACS and a logical OR gate according to an exemplary embodiment.

In a further embodiment, and referring again to FIG. 1, the system clock 130 can calculate the sampled evoked biological signal by sampling and holding the evoked biological signal at a predetermined rate. In this embodiment, the modulator 124 can modulate the sampled evoked biological signal by multiplying the sampled evoked biological signal with the carrier sequence code using a logical XOR gate. Further, the demodulator 126 can demodulate the modulated evoked biological signal by calculating the convolution of the modulated evoked biological signal with the carrier sequence code. Referring again to the illustrative example, the demodulator can calculate the convolution of $B_{7d}$=(1,1, 1,0,0,1,0) with $AB_7$=($a_1$, $a_2$, $a_3$, $-a_4$, $-a_5$, $a_6$, $-a_7$) using a logical XOR gate, the result of which is $(B_{7dac})$=(1,1,2,3,3, 3,4,3,3,3,2,1,1). In this example, the resulting evoked biological signal spectrum has an amplitude of 4A with sidebands of 3, 2, or 1, and a peak to sideband ratio of 4/26. FIG. 3B is a schematic diagram of exemplary biological signal convolution using HACS and a logical XOR gate according the example described above.

Figure 4:
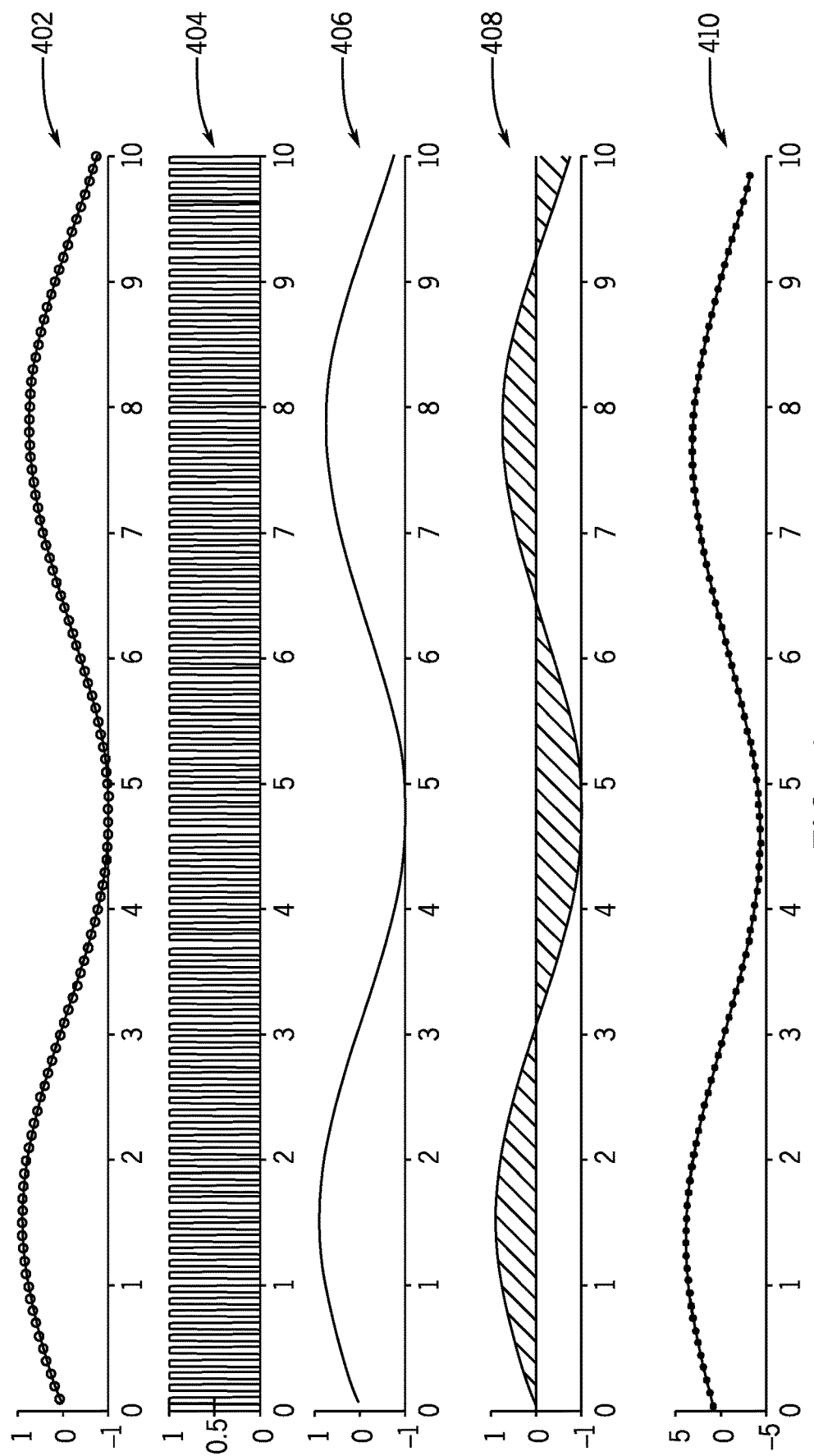
FIG. 4 is a schematic diagram of exemplary biological signal traces modulated and demodulated using HACS according to an exemplary embodiment.

The embodiment discussed in FIG. 3B is shown graphically in FIG. 4. Specifically, FIG. 4 illustrates exemplary biological signal traces modulated and demodulated using HACS according to an exemplary embodiment. Trace 402 illustrates a sinusoidal signal, for example, an evoked biological signal. The sinusoidal signal is discretized by sampling and holding the signal according to the system clock at predetermined rate shown in trace 404. The result of which is shown in trace 406. Trace 408 illustrates the modulation of the sampled evoked biological signal by multiplying the sampled evoked biological signal with the carrier sequence code using a logical XOR gate. Trace 410 illustrates the demodulation of the modulated evoked biological signal by convolving the modulated evoked biological signal with the carrier sequence code. As can be seen in trace 410, the amplification is 4A.

Referring again to FIG. 1, based on a peak to sideband ratio, a true evoked biological signal can be reconstructed. Specifically, the filter 128 communicatively coupled to the sensor 104, can calculate deviations between the sampled evoked biological signal and the peak to sideband ratio. The filter 128 can filter and/or tune noise artifacts from the sampled evoked biological signal based on the deviations, and output a true evoked biological signal based on the filtering. For example, the filter 128 can remove elements of the sampled evoked biological signal if the respective deviation meets a predetermined threshold outside of the peak to sideband ratio. In one embodiment, the deviation of each element of the sampled evoked biological signal is compared to a predetermined threshold. The filter 128 can filter respective elements of the sampled evoked biological signal based on the comparison.

Referring again to the illustrative example shown in FIG. 2, the peak to sideband ratio is -7/6. Thus, elements of the sampled evoked biological signal that diverge more than a predetermined threshold from the peak to sideband ratio of −7/6 are rejected and removed. For example, if an element of the sampled evoked biological signal diverges more than one part in 1000 from the −7/6 peak to sideband ratio, this element is removed. In one embodiment, this element is removed and replaced with the last continuous value in the sampled evoked biological signal. Thus, a true evoked biological signal can be reconstructed by filtering out said deviations.

Figure 5:
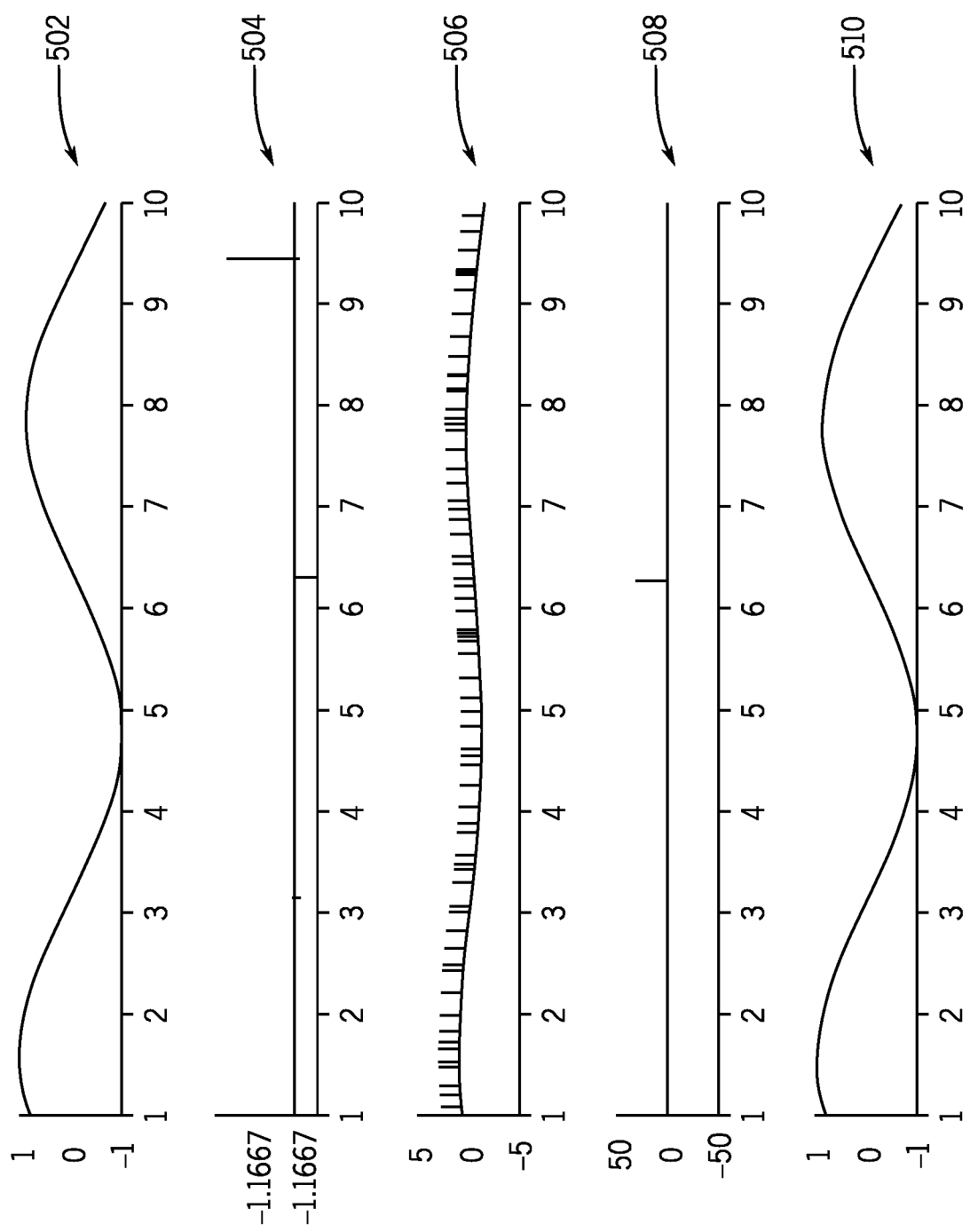
FIG. 5 is a schematic diagram of exemplary biological signal traces with simulated "spiky" noise added modulated and demodulated using HACS according to another exemplary embodiment.

Referring now to FIG. 5, an illustrative example of using HACS to filter noise using the evoked biological signal spectrum is shown. In particular, FIG. 5 illustrates exemplary biological signal traces with simulated "spiky" noise added modulated and demodulated using HACS according to another exemplary embodiment. Trace 502 illustrates a sinusoidal signal, for example, a true evoked biological signal with little to no noise. Trace 504 illustrates the evoked biological signal with noise added at a noise to signal ratio of approximately 2. Trace 506 illustrates the evoked biological signal spectrum with a peak to sideband ratio of −7/6. Trace 508 illustrates the introduction of spikey random noise to the signal shown in trace 502 with a divergence from the peak to sideband ratio. Based on the divergence from the peak to sideband ratio, the noise shown in trace 508 is removed and the signal shown in trace 502 is reconstructed as shown in trace 510. Similar peak to sideband deviation rejection criterion can be used with the AND and XOR logic gates of FIG. 3A and FIG. 3B to similarly reject noisy data points.

FIGS. 6A and 6B illustrate the application of HACS in a real world application. In FIG. 6A, trace 602 illustrates an evoked biological signal, a PPG signal, measured in a real world environment via direct skin contact with a sensor, which shows little noise. Trace 604 illustrates a recording of PPG signals made simultaneously with trace 602 using a non-contact sensor, thereby introducing a considerable amount of ambient noise. In FIG. 6B, trace 606 illustrates an evoked biological signal, a PPG signal, measured in a real world environment via direct skin contact with a sensor, which as can be seen, shows little noise. Trace 608 illustrates modulation and demodulation of the evoked (non-contact) biological signal at a 4 ms sampling rate using HACS. Accordingly, by varying the predetermined sampling rates, the peak to sideband ratio can be optimized, which results in less noise artifacts in the signal, for example see trace 608 as compared to trace 604. Thus, the use of HACS for recording biological signals as described herein shows the reduction of noise and/or motion artifacts to reconstruct a true biological signal.

Referring again to FIG. 1, in some embodiments, the predetermined sampling rate controlled by the system clock 130 can be varied to reduce noise in a signal. In some embodiments, the sampling rate can be tuned so that the frequency of the sample is increased and/or decreased. For example, a sampling interval of 2 ms can be tuned to a sampling rate of 4 ms. Further, the predetermined sampling rate can be held by the system clock 130 according to the peak to sideband ratio. This results in minimized sideband deviations.

Another exemplary operation of system 100 shown FIG. 1 will now be described. As discussed above, in one embodiment, the system 100 includes the sensor 104 with the transmitter 108. The transmitter 108 transmits control signals according to a carrier sequence code to the transmission source 110. Thus, the transmission source 110 transmits energy (i.e., energy wave 120) towards the subject 106 according to the carrier sequence code. The carrier sequence code has an autocorrelation function. In this embodiment, the carrier sequence code can be converted into binary format.

For example, the carrier sequence code $B_7=(1, 1, 1, -1, -1, 1, -1)$ can be converted and/or modified to binary format as $B_{7d}=(1,1,1,0,0,1,0)$. According to the binary format of the carrier sequence code, the transmission source 110 is flashed (e.g., blinked) ON (i.e., 1) and OFF (i.e., 0). Further, the sensor 104 includes the receiver 112 to receive an evoked biological signal 122 in response to energy reflection returned from the subject 106. The evoked biological signal 122 is an analog signal and modulated according to the carrier sequence code. As an illustrative example using $B_{7d}$, if the transmission source 110 is ON, the output is S+N where S is the signal and N is the noise. If the transmission source is OFF, the output is N. Accordingly, the evoked biological signal modulated according to $B_{7d}$ is equal to (S+N, S+N, S+N, N, N, S+N, N).

The demodulator 126 communicatively coupled to the sensor 104, receives, the modulated evoked biological signal and demodulates the modulated evoked biological signal by calculating a convolution of the evoked biological signal with the carrier sequence code resulting in an evoked biological signal spectrum. In this example, the modulated biological signal is convolved with $B_7=(1,1,1,-1,-1,1,-1)$. The evoked biological signal spectrum has signal-to-noise ratio proportional to a peak to sideband ratio and the peak to sideband ratio is a function of the carrier sequence code. In this example, the peak to side band ratio is 4/−3, and can be expressed as 4(S+N)−3N=4S+N.

Figure 7:
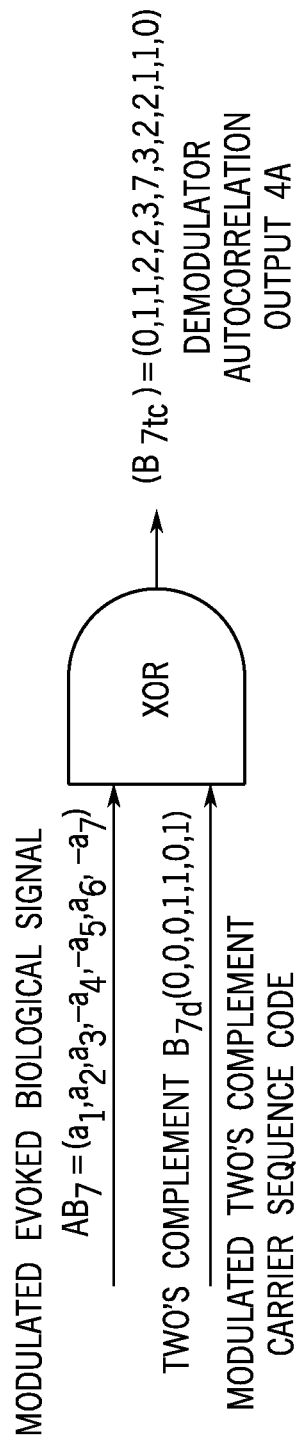
FIG. 7 is a schematic diagram of exemplary biological signal convolution using a two's complement HACS and a logical XOR gate according to an exemplary embodiment.

In another embodiment, the transmission source 110 can be flashed using the carrier sequence code and the modulated evoked biological signal can be convolved with a two's complement of the carrier sequence code. For example, the modulated biological signal is convolved using a logical XOR gate with the two's complement of $B_7=(1,1,1,-1,-1,1,-1)$, which is $B_{7d}=(0,0,0,1,1,0,1)$. The resulting evoked biological spectrum is $B7_{tc}=(0,1,1,2,2,3,7,3,2,2,1,1,0)$. Here, the amplification is 7A with sidebands slightly greater than 2. FIG. 7 is a schematic circuit diagram of the demodulator 126 of FIG. 1 using a logical XOR gate according the example described above.

Figure 8:
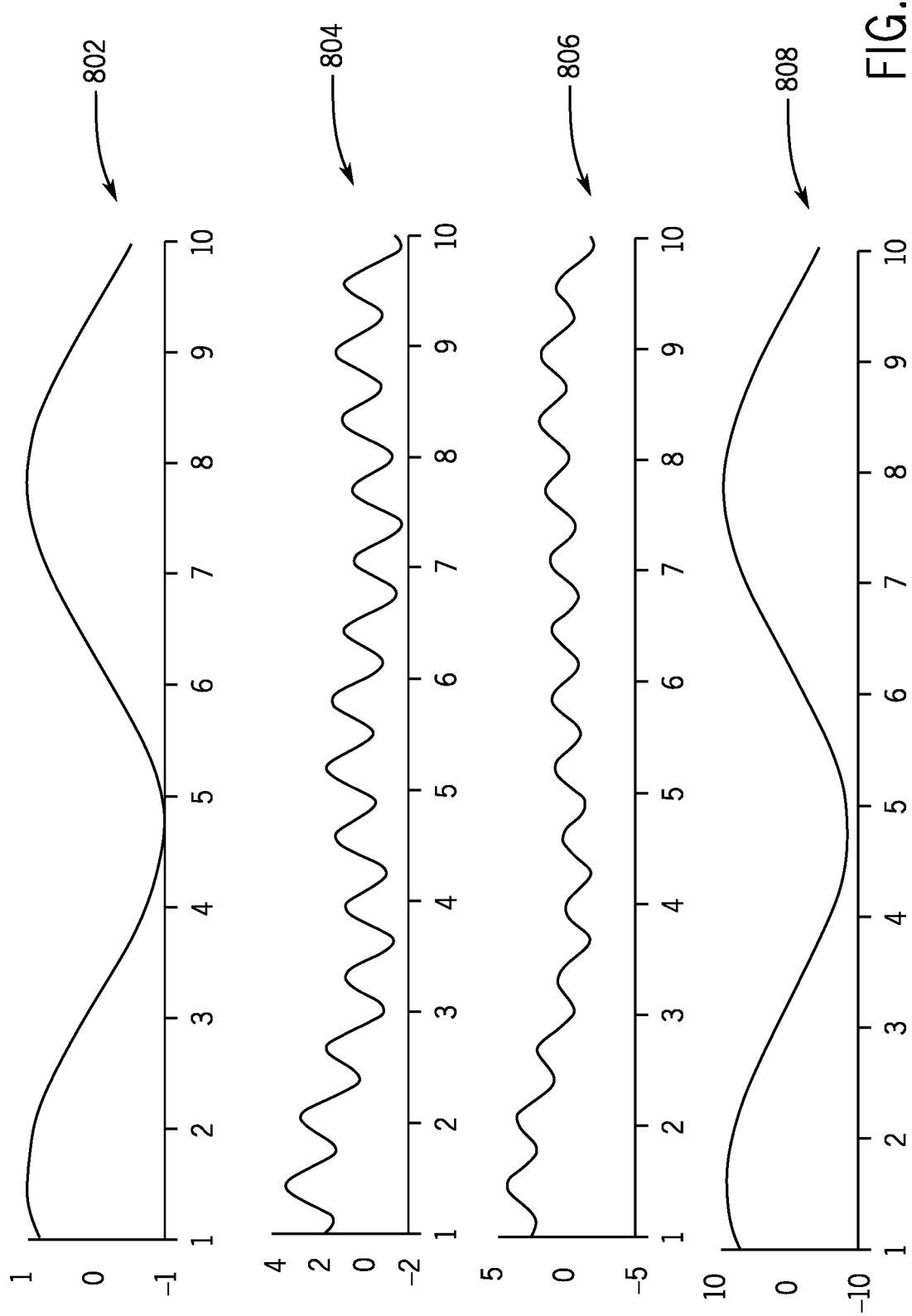
FIG. 8 is a schematic diagram of exemplary biological signal traces with sinusoidal noise sources in which sidebands of the noise overlap the sidebands of the signals, modulated and demodulated using HACS according to a further exemplary embodiment.

In a further embodiment, modulation of the carrier sequence code can use concatenation of two carrier sequences codes each having a different length. For example, the Barker code with length seven (7) can be concatenated with the Barker code of length 11. Converted into binary format, this results in $B_{711d}=(1,1,1,0,0,1,0,1,1,1,0,0,0,1,0,0,1,0,)$. Accordingly, the transmission source 110 can be flashed according the concatenated carrier sequence code in binary format. The demodulator 126 calculates the convolution of the modulated evoked biological signal with the concatenated carrier sequence code, $B_{711}=(1,1,1,-1,-1,1,-1,1,1,1,-1,-1,1,1,-1,-1,1,-1)$. In this example, the peak to side band ratio is 9, and can be expressed as 9(S+N)−9N=9S. Thus, in this example, the system noise is completely rejected. This example is shown graphically in FIG. 8. More specifically, FIG. 8 illustrates exemplary biological signal traces with sinusoidal noise sources in which sidebands of the noise overlap the sidebands of the signals, modulated and demodulated using HACS according to a further exemplary embodiment. Trace 802 illustrates a sinusoidal signal, for example, an evoked biological signal S=sin(x). Trace 804 illustrates noise and/or motion artifacts as N=sin(0.5x)+sin(x)+sin(1.5x)+sin(10x). Trace 806 illustrates the signal with noise, S+N. Trace 808 illustrates the convolution product spectrum of the evoked biological signal with amplification of 9. The demodulator 126 and/or the filter 128 can further process the modulated evoked biological signal by generating a true evoked biological signal by extracting the true evoked biological signal from the modulated evoked biological signal based on the peak to sideband ratio.

Figure 9:
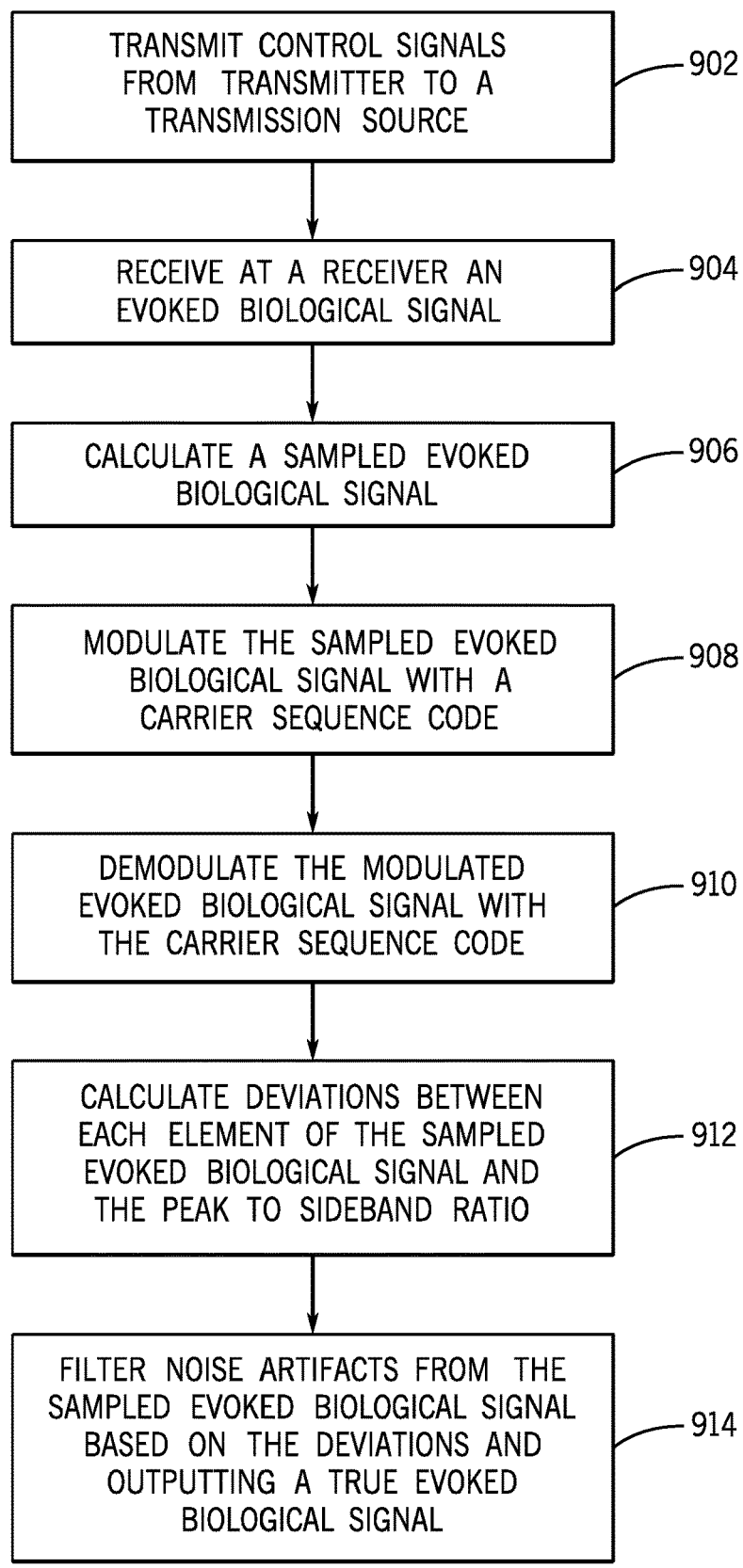
FIG. 9 is a flow diagram of an exemplary method for biological signal processing using highly auto-correlated carrier sequence codes (HACS) according to an exemplary embodiment.

Referring now to FIG. 9, an exemplary method for biological signal recording using highly auto-correlated carrier sequence codes (HACS) according to an a exemplary embodiment will be described. FIG. 9 will be described with reference to the components of FIGS. 1-3. The methods described herein can be facilitated by the system components and examples described above. At block 902, the method includes transmitting control signals from a transmitter of a sensor to a transmission source. The transmission source transmits energy towards a subject according to the control signals. As discussed above with FIG. 1, the transmitter 108 controls the transmission source 110. More specifically, the transmitter 108 transmits control signals (not shown) to the transmission source 110 and the transmission source 110 transmits energy (e.g., a energy signal 120) towards the subject 106 according to the control signals.

At block 904, the method includes receiving at a receiver of the sensor an evoked biological signal in response to energy reflection returned from the subject. The evoked biological signal is an analog signal. As discussed above with FIG. 1, the receiver 112 receives an evoked biological signal 122 representing a biological measurement (e.g., a PPG measurement) of the subject 106. At block 906, the method includes calculating a sampled evoked biological signal by sampling the evoked biological signal at a predetermined sampling rate. The sampled evoked biological signal can be expressed in vector form as $A=(a_1, a_2, a_3, a_4, a_5, a_6, a_7 \ldots)$ where A represents the evoked biological signal 122 and each element in A represents $A(i_t)$, where t is the sampling rate and/or sampling interval. The system clock 130 controls sampling of the evoked biological signals at different sampling rates. In some embodiments, as discussed above, calculating the sampled evoked biological signal further includes sampling and holding the evoked biological signal by the system clock 130 at a predetermined rate.

Further, at block 908, the method includes modulating the sampled evoked biological signal with a carrier sequence code resulting in a modulated evoked biological signal. The carrier sequence code has an autocorrelation function. The carrier sequence code can be a highly auto-correlated carrier sequence (HACS) to process the evoked biological signal. For example, as described in the exemplary embodiments herein, the carrier sequence code can be a Barker code of length seven (7). As discussed above, in some embodiments, the modulator 124 can facilitate the modulation of the sampled evoked biological signal according to HACS. For example, the sampled evoked biological signal multiplied by Barker Code $B_7$ results in modulation of the sampled evoked biological signal, which is expressed in vector format as $AB_7=(a_1, a_2, a_3, -a_4, -a_5, a_6, -a_7)$.

As discussed above, in some embodiments, modulating the sampled evoked biological signal further includes converting the carrier sequence code to binary format and modulating the sampled evoked biological signal with the carrier sequence code in binary format. Thus, the carrier sequence code $B_7=(1, 1, 1, -1, -1, 1, -1)$ can be converted to binary format as $B_{7d}=(1,1,1,0,0,1,0)$. Additionally, in embodiments where the sampled evoked biological signal is sampled and held, modulating the sampled evoked biological signal can include multiplying the sampled evoked biological signal with the carrier sequence code using a logical XOR gate. (See FIGS. 7 and 8).

At block 910, the method includes demodulating the modulated evoked biological signal by calculating a convolution of the modulated evoked biological signal with the carrier sequence code resulting in an evoked biological signal spectrum. The evoked biological signal spectrum has a peak to sideband ratio as a function of the carrier sequence code. In other embodiments, the evoked biological signal spectrum represents the evoked biological signal with amplitude increased by a factor proportional to the peak to sideband ratio. As discussed above, according to one illustrative example, the demodulator 126 can convolve $AB_7=(a_1, a_2, a_3, -a_4, -a_5, a_6, -a_7)$ with the original Barker code used for modulation, for example, Barker Code $B_7$, which results in an evoked biological signal spectrum with a peak to sideband ratio equal to 7A/−6.

In examples where the sampled evoked biological signal is modulated using a carrier sequence code in binary format, demodulating the modulated evoked biological signal further includes demodulating the modulated evoked biological signal by calculating the convolution of the modulated evoked biological signal with the carrier sequence code in binary format using a logical AND gate. For example, FIG. 3A illustrates exemplary biological signal convolution using HACS and a logical AND gate.

At block 912, the method includes calculating deviations between each element of the sampled evoked biological signal and the peak to sideband ratio. For example, the filter 128 can calculate deviations between the sampled evoked biological signal and the peak to sideband ratio. At block 914, the method includes filtering noise artifacts from the sampled evoked biological signal based on the deviations and outputting a true evoked biological signal based on the filtering. Thus, in one embodiment, the filter 128 can filter noise artifacts from the sampled evoked biological signal based on the deviations, and output a true evoked biological signal based on the filtering.

Figure 10:
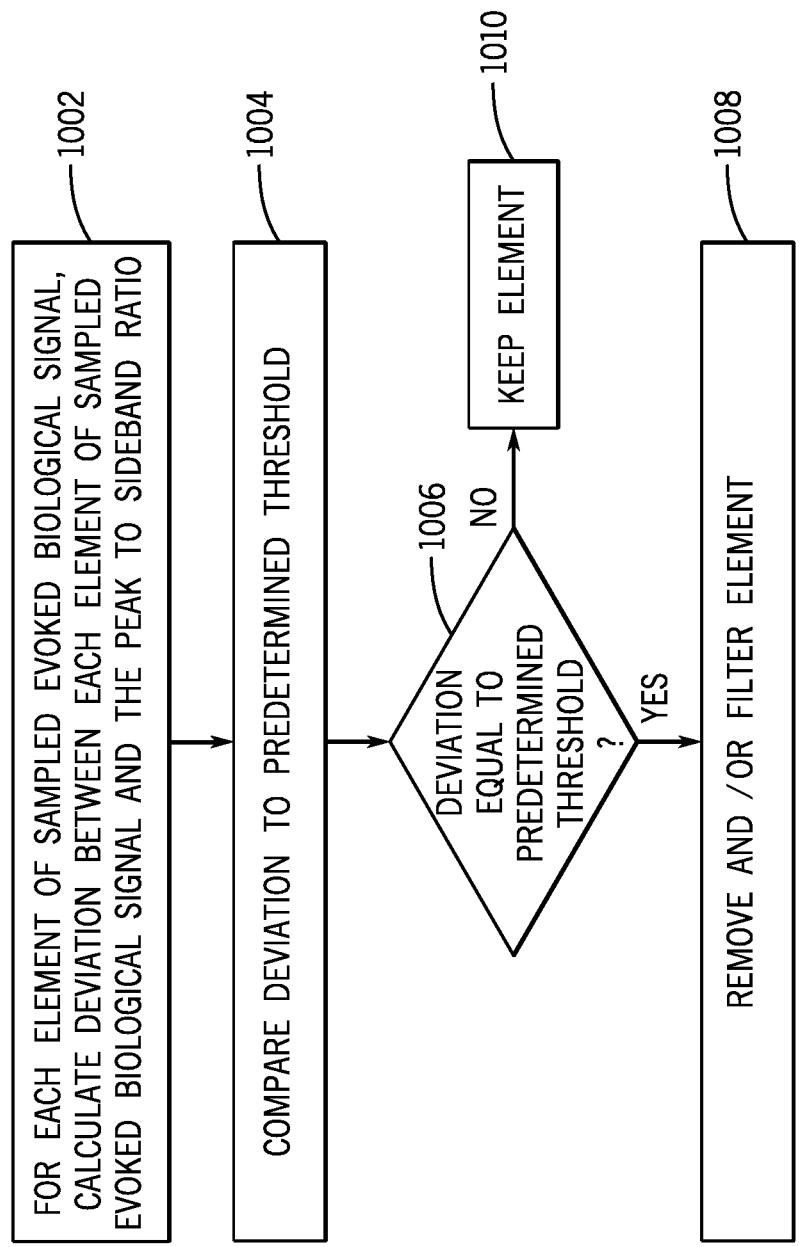
FIG. 10 is a flow diagram of an exemplary method for filtering the modulated evoked biological signal according to an exemplary embodiment.

Calculating deviations and filtering noise artifacts will now be described in more detail with reference to FIG. 10. As mentioned above, for each element of the modulated biological signal, the deviation between each element and the peak to sideband ratio is determined at block 1002. At block 1004, the deviation is compared to a predetermined threshold. At block 1006, if the deviation meets and/or equals the predetermined threshold, then at block 1008, the respective element of the sampled evoked biological signal is removed. In one embodiment, this element is removed and replaced with the last continuous value in the sampled evoked biological signal. Otherwise, at block 1010, the respective element of the sampled evoked biological signal is not removed.

Figure 11:
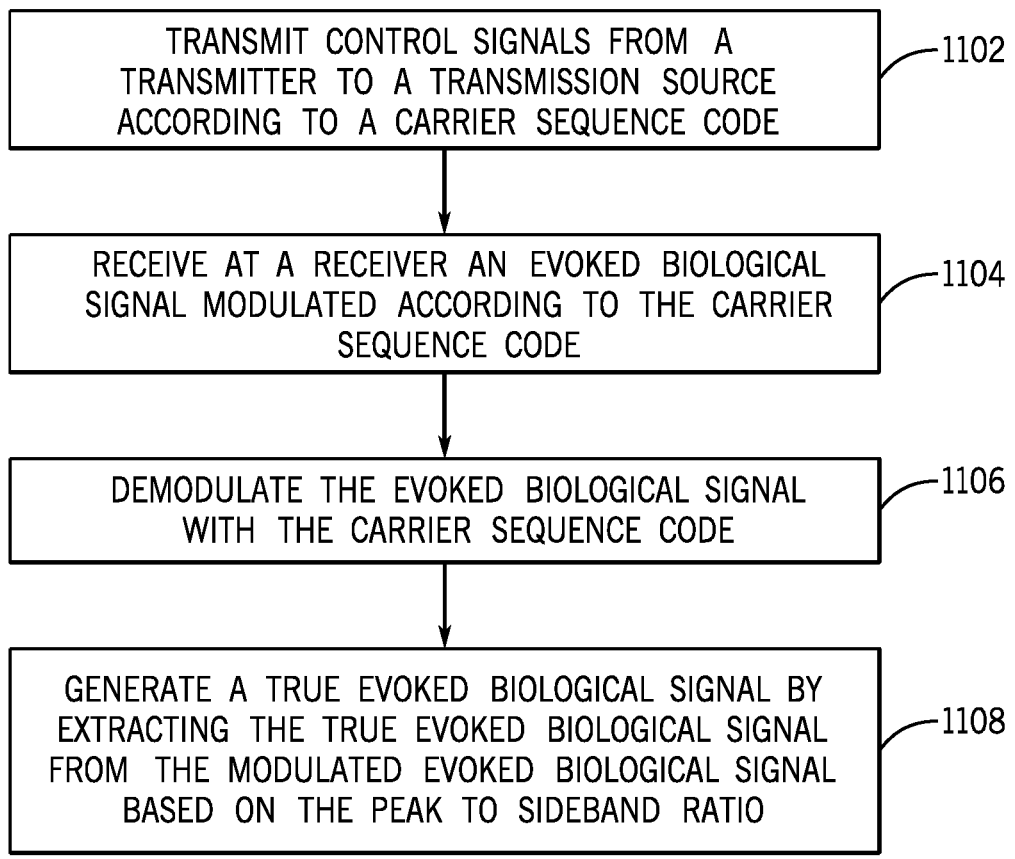
FIG. 11 is a flow diagram of a different exemplary method for biological signal processing using highly auto-correlated carrier sequence codes (HACS) according to an exemplary embodiment.

Referring now to FIG. 11, an exemplary method according to another embodiment for biological signal recording using highly auto-correlated carrier sequence codes (HACS) will be described. At block 1102, the method includes transmitting control signals from a transmitter of a sensor to a transmission source. The control signals are transmitted according to a carrier sequence code and the transmission source transmits energy towards a subject according to the carrier sequence code. The carrier sequence code has an auto correlation function. Thus, in one embodiment, transmitting control signals from the transmitter 108 of the sensor 104 to the transmission source 110 includes the control signals driving the execution and/or command (e.g., ON/OFF, blinking) of the transmission source 110 according to the carrier sequence code. In some embodiments, as discussed above, the carrier sequence code is a concatenation of two carrier sequences codes each having a different length.

At block 1104, the method includes receiving at a receiver of the sensor an evoked biological signal in response to energy reflection returned from the subject. The evoked biological signal is an analog signal and modulated according to the carrier sequence code. Thus, the sensor the sensor 104 includes the receiver 112 to receive an evoked biological signal 122 in response to energy reflection returned from the subject 106.

At block 1106, the method includes demodulating the evoked biological signal by calculating a convolution of the evoked biological signal with the carrier sequence code resulting in an evoked biological signal spectrum. The evoked biological signal spectrum has a signal-to-noise ratio proportional to a peak to sideband ratio. The peak to sideband ratio is a function of the carrier sequence code. In some embodiments, as discussed above, the carrier sequence code is a concatenation of two carrier sequences codes each having a different length. Thus, the demodulation is performed by convolving the modulated biological signal with the concatenation of two carrier sequence codes. In a further embodiment, demodulating the modulated evoked biological signal further includes demodulating the modulated evoked biological signal by calculating the convolution of the modulated evoked biological signal with a two's complement of the carrier sequence code in binary format using a logical XOR gate. (See FIG. 7). Further, at block 1108, the method includes generating a true evoked biological signal by extracting the true evoked biological signal from the modulated evoked biological signal based on the peak to sideband ratio. Accordingly, a true biological signal can be reconstructed from a noisy environment.

Figure 12:
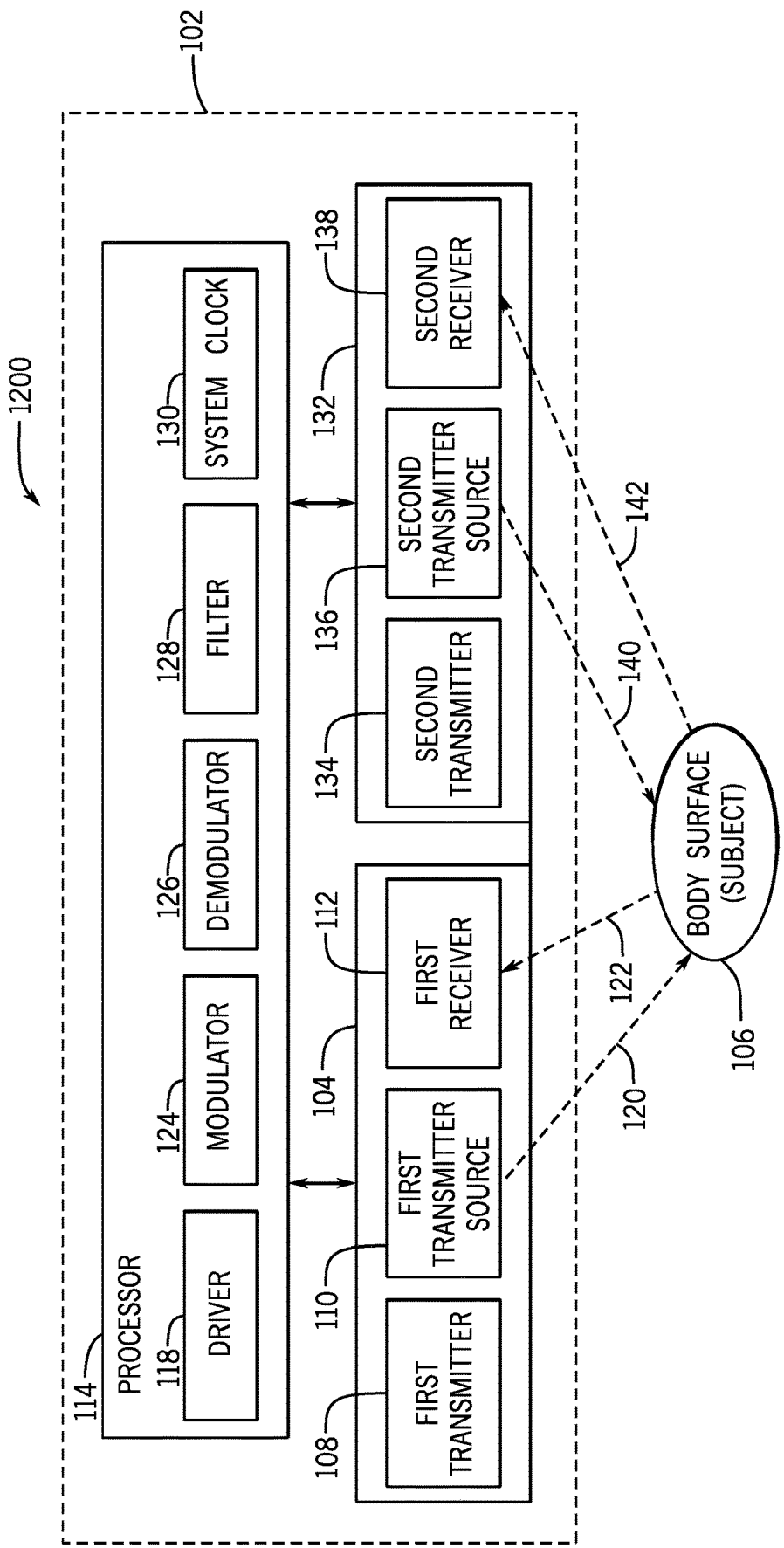
FIG. 12 is an exemplary block diagram of a system for biological signal processing using highly auto-correlated carrier sequence codes (HACS) according to another exemplary embodiment.

As discussed above with FIG. 1, in some embodiments, the system 100 can include more than one sensor. In some embodiments, the additional sensor can be utilized for noise cancellation to remove unwanted noise artifacts and obtain a true biological signal in a noisy environment. Referring now to FIG. 12, a system 1200 for biological signal recording using highly auto-correlated carrier sequence codes (HACS) according to another exemplary embodiment will be discussed. For simplicity, like numerals and components in FIG. 12 represent the same or similar elements discussed in detail with FIG. 1. Further, the components FIG. 12, as well as the components of other systems, hardware architectures, and software architectures discussed herein, can be combined, omitted, or organized into different architectures for various embodiments. In some embodiments, the components of the system 1200 can be implemented within a vehicle 102, for example, as discussed in U.S. application Ser. No. 14/697,593, now published as U.S. 2015/0229341, which is expressly incorporated herein by reference.

In FIG. 12, the system 1200 includes two sensors, namely, a first sensor 104 and a second sensor 132. As discussed above in detail with FIG. 1, the first sensor 104 is a sensor for detecting plethysmograph (PPG) measurements from a body surface of a subject 106. In particular, the first sensor 104 can measure changes in transmission or diffused reflectance from the body surface (e.g., body tissue) of the subject 106 under active illumination. Accordingly, the first sensor 104 can include a first transmitter 108, a first transmission source 110, and a first receiver 112. The first transmission source 110 can include at least one light source (e.g., light emitting diode (LED), laser, laser diode) that can transmit light of a particular wavelength. In the embodiments discussed herein, which will be used as an illustrative example, the first transmission source 110 transmits energy (e.g., an energy signal/wave) with high-spectrum energy. For example, the first transmission source 110 produces energy toward the subject 106 with a wavelength within the red or infrared (IR) emission spectrum. Accordingly, in this embodiment, the first transmission source 110 emits a signal corresponding to a red light (e.g., about 660 nm wavelength) or IR light (e.g., about 780-940 nm wavelength).

The second sensor 132 is a sensor for detecting a signal, which is predominantly noise, from the body surface of the subject 106. This signal can be used for adaptive and active noise cancellation. In FIG. 12, the second sensor 132 includes a second transmitter 134, a second transmission source 136, and a second receiver 138. The second transmission source 136 can include at least one light source (e.g., light emitting diode (LED), laser, laser diode) that can transmit light of a particular wavelength. In particular, in the embodiments discussed herein, which will be used as an illustrative example, the second transmission source 136 transmits energy (e.g., an energy signal/wave) with low-spectrum energy. Thus, the second transmission source 136 produces energy toward the subject 106 with a wavelength within the blue emission spectrum. For example, in some embodiments, the second transmission source 136 emits a signal corresponding to a blue light having a wavelength of about 420-495 nm. Based on the above, the second transmission source 136 produces energy in an emission spectrum that is different than the emission spectrum of the energy produced by the first transmission source 110. In particular, the second transmission source 136 produces non-red light energy having low-spectrum energy.

As discussed above in detail with FIG. 1, the processor 114 can include a driver 118 which controls the first transmitter 108 and/or the first transmission source 110. The driver can also control the second transmitter 134 and/or the second transmission source 136. In other embodiments, the driver 118 can be a component of the first sensor 104 and/or the second sensor 132. In the embodiment shown in FIG. 12, the first transmitter 108 and/or the driver 118 can cause the first transmission source 110 to drive energy based on a pulsed basis. In the embodiments discussed herein, the illumination (e.g., energy wave) can be pulsed (e.g., blinked) according to a carrier sequence code with an autocorrelation function. In FIG. 12, the energy wave transmitted to the subject 106 from the first transmission source 110 is indicated by the dashed line 120. For simplicity, in the examples discussed herein, the energy wave indicated by the dashed line 120 will be referred to as an IR energy wave 120. The second transmitter 134 and/or the driver 118 can cause the second transmission source 136 to drive energy on a continuous basis (e.g., not pulsed, not blinked). In FIG. 12, the energy wave transmitted to the subject 106 from the second transmission source 136 is indicated by the dashed line 140. For simplicity, in the examples discussed herein, the energy wave indicated by the dashed line 140 will be referred to as a blue energy wave 140.

Upon transmission of the IR energy wave 120 and/or the blue energy wave 140 towards the subject 106, energy is reflected from the subject 106 and received by the first receiver 112 and/or the second receiver 138. In FIG. 12, the reflected energy received by the first receiver 112 is an evoked biological signal and is indicated by the dashed line 122. As discussed above in detail, the evoked biological signal 122 is in analog form. The reflected energy received by the second receiver 138 is an evoked noise signal and is indicated by the dashed line 142. The evoked noise signal 142 is a signal that predominantly captures noise and/or motion artifacts. It is understood that the evoked biological signal 122 can also include noise and/or motion artifacts including residual energy reflected in response to the blue energy wave 140. This is because the IR energy wave 120 is transmitted on a pulsed basis and the blue energy wave 140 is transmitted continuously. Additionally, it is understood that the evoked noise signal 142 can also include noise and/or motion artifacts including residual energy reflected in response to the IR energy wave 120. As will be discussed in detail herein, the processor 114 and/or the filter 128 can perform noise cancellation processing using the evoked biological signal 122 and the evoked noise signal 142 to remove unwanted noise artifacts from the evoked biological signal 122.

Figure 13A:
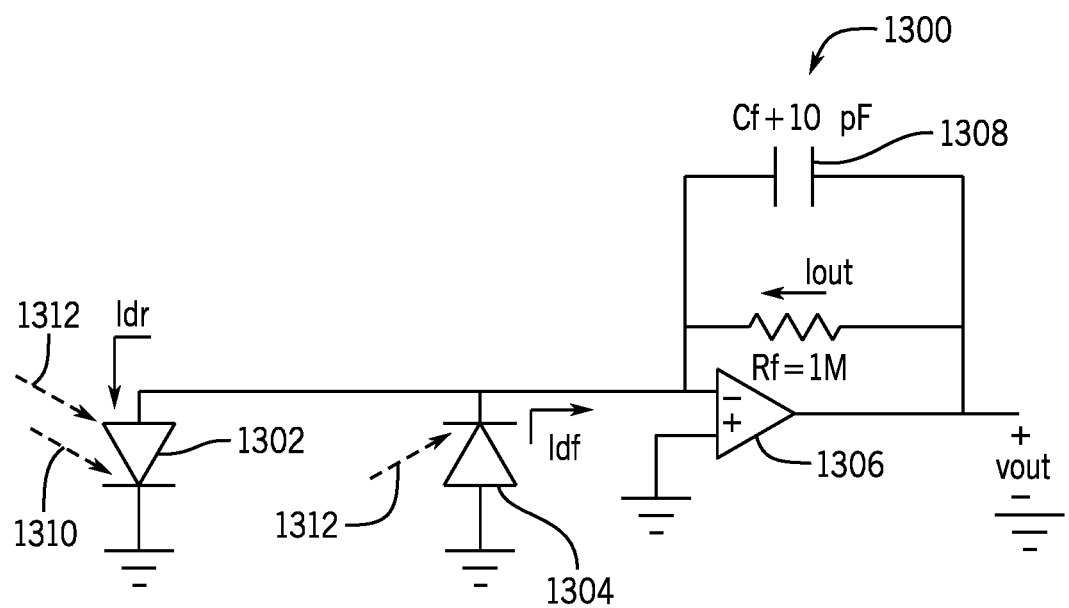
FIG. 13A is an exemplary circuit diagram of the first receiver and the second receiver of the system shown in FIG. 12.

Signal noise cancellation using the evoked biological signal 122 and the evoked noise signal 142 using the blue light technology will now be described in more detail with reference to FIG. 13A and FIG. 13B. FIG. 13A is an exemplary circuit diagram 1300 illustrating the noise cancellation process according to an exemplary embodiment. In FIG. 13A, the circuit diagram 1300 includes a first photodiode 1302, a second photodiode 1304, an operational amplifier 1306, and a feedback capacitor (CF) 1308. In some embodiments, the first photodiode 1302 can be part of the first sensor 104, for example, as part of the first receiver 112. In FIG. 13A, the first photodiode 1302 receives reflected energy 1310 in response to the IR energy wave 120 and reflected energy 1312 in response to the blue energy wave 140. Accordingly, the evoked biological signal 122 is a measurement of the reflected energy 1310 and the reflected energy 1312. Thus, the evoked biological signal 122 includes IR light signal components (e.g., PPG signals) and blue light signal components (e.g., noise). In FIG. 13A, the reflected energy 1310 and the reflected energy 1312 received by the first photodiode 1302 generates a reverse diode current (Idr).

In some embodiments, the second photodiode 1304 can be part of the second sensor 132, for example, as part of the second receiver 138. In FIG. 13A, the second photodiode 1304 receives reflected energy 1312 in response to the blue energy wave 140. This is because the IR energy wave 120 is transmitted on a pulsed basis and the blue energy wave 140 is transmitted continuously. Thus, when the IR energy wave 120 is pulsed OFF, reflected energy in response to the IR energy wave 120 is not received by the second receiver 138 and/or the second photodiode 1304. Accordingly, the evoked noise signal 142 includes blue light signal components (e.g., noise). In FIG. 13A, the reflected energy 1312 received by the second photodiode 1304 generates a forward diode current (Idf).

As mentioned above, the circuit diagram 1300 also includes the operational amplifier 1306, however, it is understood that other types of amplifiers and/or hardware for signal processing can be implemented. In some embodiments, the operational amplifier 1306 is included as a component of the filter 128. Since the positive input to the operational amplifier 1306 is grounded, the negative input will also be at ground. The current flowing into a negative terminal of the operational amplifier 1306 is zero. The current flowing across the feedback capacitor (Cf) 1308 is negligible. Therefore, the output current (Iout) of the operational amplifier 1306 is equal to the difference of the reverse diode current and the forward diode current (i.e., Idr−Idf). Furthermore, the output voltage of the operational amplifier 1306 is equal to the output current multiplied by Rf. More specifically, the output voltage (Vout) can be expressed mathematically as:

$$V_{out}=I_{out}*R_f \quad (1)$$

As will be described in more detail herein, noise artifacts from the evoked biological signal 122 can be filtered using the evoked noise signal 142 according to the configuration of the circuit 1300 shown in FIG. 13A. In the embodiments discussed herein, signal cancellation of common mode is used to remove noise artifacts from the evoked biological signal 122. Referring again to FIG. 13A, the reverse diode current (Idr) includes energy 1310 in response to the IR energy wave 120 and reflected energy 1312 in response to the blue energy wave 140, including noise. Accordingly, in this embodiment, Idr=blue light current (IBL)+red light current (IRL)+noise (N). The forward diode current (Idf) includes reflected energy 1312 in response to the blue energy wave and noise. Thus, Idf is equal to (IBL+IN). Using signal cancellation, the output current (Iout) is equal to (Idr−Idf), and thus equal to IRL. Thus, the output current (Iout) provides a signal that removes the common mode between the two signals and the RL energy remains in the output current (Iout). Said differently, the output current (Iout) can be expressed mathematically as:

$$I_{out}=(IBL+IRL+N)-(IBL+N) \quad (2)$$

Figure 13B:
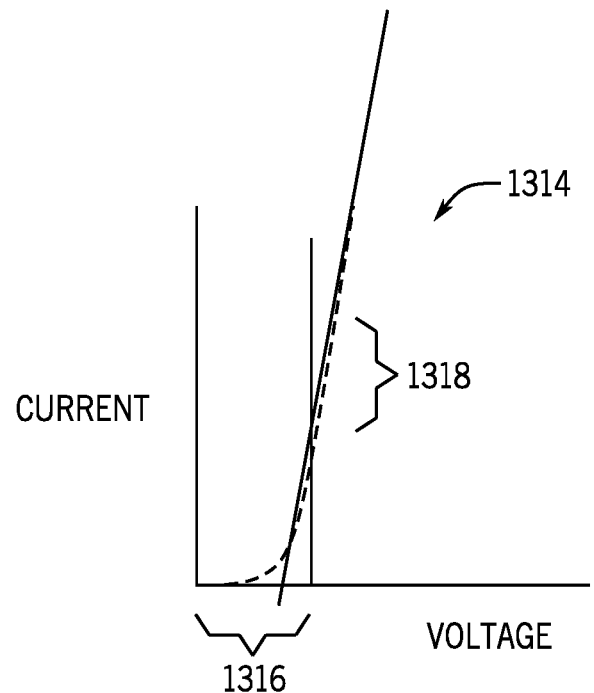
FIG. 13B is a graph illustrating the transfer characteristics between voltage (Vo) and current (Vi) with respect to the circuit of FIG. 13A according to an exemplary embodiment.

The effects of using signal cancellation as described above can be further visualized using the graph 1314 shown in FIG. 13B. The graph 1314 illustrates the diode transfer characteristics between current and voltage (diode IV transfer function). By using the second sensor 132 transmitting a low-spectrum energy wave (e.g., blue energy wave 140), a bias voltage 1316 is kept on the reverse diode current so that when the first sensor 104 transmits a pulsed high-spectrum energy (e.g., IR energy wave 120), the first photodiode 1302 will deliver a current from the linear range 1318 of the IV curve. Further, the blue energy wave 140 puts the same current on the forward diode and also some noise N. Thus, having the diodes oriented at opposite polarities allows for signal cancellation to remove common noise artifacts from the evoked biological signal 122. The operating current range is the range over which modulation of the pulse from varying IR absorption due to the cardiac cycle. This range is comparatively small in relation to noise N and amenable to HACS modulation, which will be discussed herein.

Figure 14:
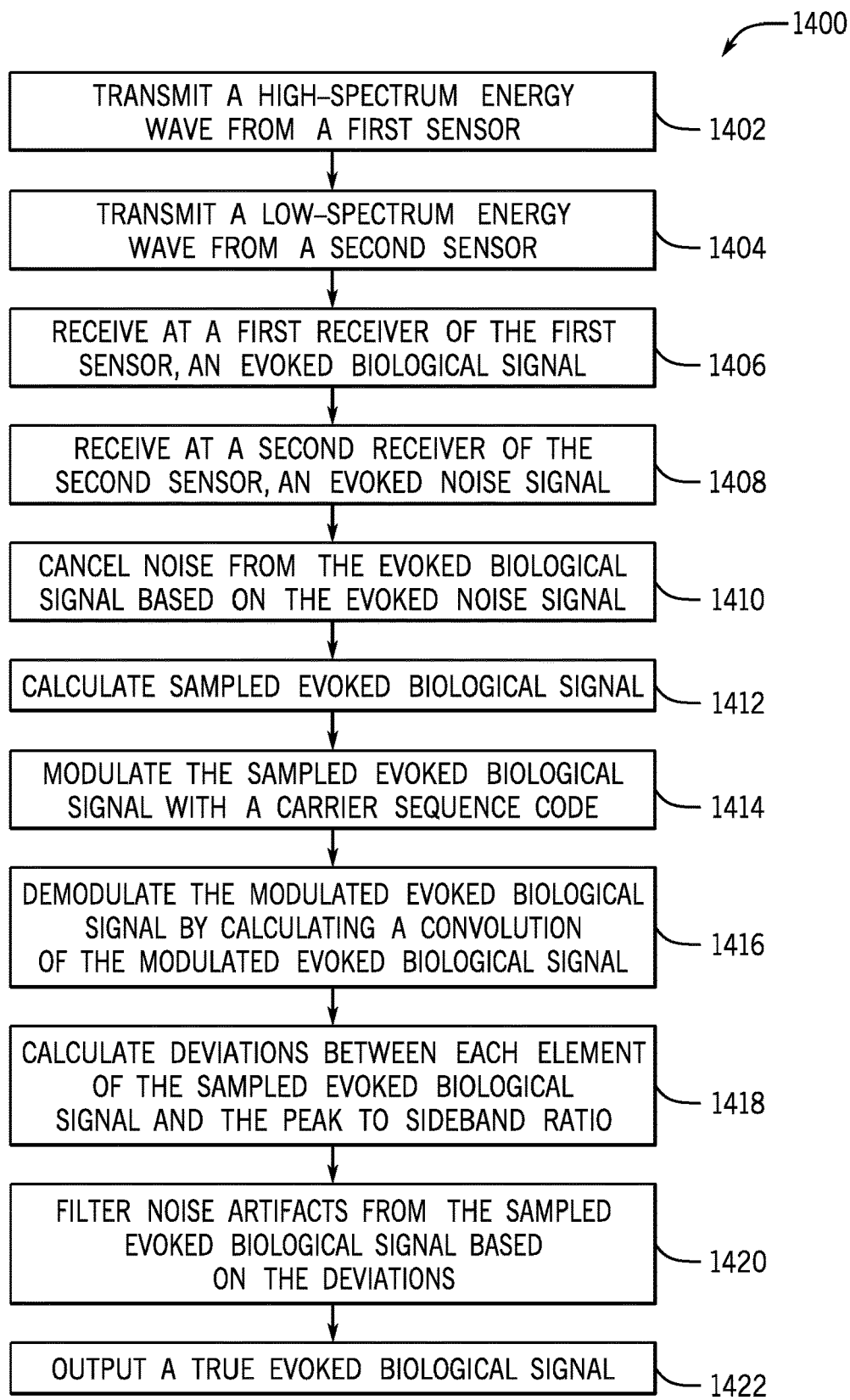
FIG. 14 is a flow diagram of an exemplary method for biological signal processing using highly auto-correlated carrier sequence codes (HACS) according to another exemplary embodiment.

Exemplary operation of the system 1200 as described with FIGS. 12, 13A, and 13B will now be further described with reference to FIG. 14. FIG. 14 is an exemplary method 1400 for biological signal recording using highly auto-correlated carrier sequence codes (HACS) according to another exemplary embodiment. In particular, the method 1400 includes noise cancellation using low-spectrum (e.g., blue light) technology. It is understood that in some embodiments, one or more of the blocks in FIG. 14 can be incorporated with one or more of the blocks in FIGS. 9 and 10. Further, some of the blocks in FIG. 14 are explained in detail with FIGS. 9 and 10.

At block 1402, the method 1400 includes transmitting a high-spectrum energy wave towards a subject from a first sensor according to a first control signal. As described with FIG. 12, the first sensor 104 includes the first transmitter 108 to transmit first control signals to the first transmission source 110. The first transmission source 110 transmits the high-spectrum energy wave 120 towards the subject 106 according to the first control signals. In one embodiment, the high-spectrum energy wave 120 is within a red color spectrum. For example, the first transmission source 110 produces energy toward the subject 106 with a wavelength within the red or infrared (IR) emission spectrum. Accordingly, in this embodiment, the first transmission source 110 emits a signal corresponding to a red light (e.g., about 660 nm wavelength) or IR light (e.g., about 780-940 nm wavelength). Further, the high-spectrum energy wave 120 can be transmitted towards the subject 106 from the first sensor 104 as a pulsed energy wave according to the first control signal. For example, the high-spectrum energy wave 120 can be transmitted according to a carrier sequence code.

At block 1404, the method 1400 includes transmitting a low-spectrum energy wave towards the subject from a second sensor according to a second control signal. As discussed with FIG. 12, the second sensor 132 is communicatively coupled to the first sensor 102. The second sensor 132 includes the second transmitter 134 to transmit second control signals to the second transmission source 136. The second transmission source 136 transmits the low-spectrum energy wave 140 towards the subject 106 according to the second control signals. In one embodiment, the low-spectrum energy wave 140 is within a blue color spectrum. Thus, the second transmission source 136 produces energy toward the subject 106 with a wavelength within the blue emission spectrum. For example, in some embodiments, the second transmission source 136 emits a signal corresponding to a blue light having a wavelength of about 420-495 nm. Based on the above, the second transmission source 136 produces energy in an emission spectrum that is different than the emission spectrum of the energy produced by the first transmission source 110. In particular, the second transmission source 136 produces non-red light energy having low-spectrum energy.

In some embodiments, the low-spectrum energy wave 140 is transmitted towards the subject 106 from the second sensor 132 as a continuous energy wave (e.g., not pulsed, not blinked) according to the second control signal. Thus, in one embodiment, the high-spectrum energy wave 120 is transmitted as pulsed energy and the low-spectrum energy wave 140 is transmitted as continuous energy.

At block 1406, the method 1400 includes receiving at a first receiver of the first sensor, an evoked biological signal from the subject. At block 1408, the method 1400 includes receiving at a second receiver of the second sensor, an evoked noise signal from the subject. As mentioned above with FIG. 12, the first sensor 102 includes the first receiver 112 to receive the evoked biological signal 122 in response to energy reflection returned from the subject 106. In the embodiments discussed herein, the evoked biological signal 122 is an analog signal. Further, the second sensor 132 includes the second receiver 138 to receive the evoked noise signal 142 in response to energy reflection returned from the subject 106. Thus, according to this embodiment, in response to transmitting the high-spectrum energy wave 120 (at block 1402) and transmitting the low-spectrum energy wave 140 (at block 1404), the method 1400 receives at the first receiver 112 of the first sensor 102 the evoked biological signal 122 at block 1406, and receives at the second receiver 138 of the second sensor 132 the evoked noise signal 142 at block 1408.

At block 1410, the method 1400 includes cancelling noise from the evoked biological signal 122 based on the evoked noise signal 142. In some embodiments, the filter 128, which is communicatively coupled to the first sensor 102 and the second sensor 132, can cancel nose from the evoked biological signal 122 based on the evoked noise signal 142. In some embodiments, cancelling noise from the evoked biological signal 122 based on the evoked noise signal 142 includes filtering the evoked biological signal 122 with the evoked noise signal 142 using signal cancellation. Thus, as described above in detail with FIGS. 13A and 13B, the signal cancellation of common mode is used to remove noise artifacts from the evoked biological signal 122. More specifically, the output current (Iout) is equal to (Idr–Idf) and can be expressed mathematically as shown in equation (2) above.

At block 1412, the method 1400 includes calculating a sampled evoked biological signal by sampling the evoked biological signal at a predetermined sampling rate. As discussed above in detail at block 906 of FIG. 9, the sampled evoked biological signal can be expressed in vector form as $A=(a_1, a_2, a_3, a_4, a_5, a_6, a_7 \ldots)$, where A represents the evoked biological signal 122 and each element in A represents $A(i_t)$, where t is the sampling rate and/or sampling interval. The system clock 130 controls sampling of the evoked biological signals at different sampling rates. In some embodiments, as discussed above, calculating the sampled evoked biological signal further includes sampling and holding the evoked biological signal by the system clock 130 at a predetermined rate.

At block 1414, the method 1400 includes modulating the sampled evoked biological signal with a carrier sequence code resulting in a modulated evoked biological signal. In some embodiments, the carrier sequence code has an auto-correlation function. As discussed above in detail with block 908 of FIG. 9, the carrier sequence code can be a highly auto-correlated carrier sequence (HACS) to process the evoked biological signal. In some embodiments, the modulator 124 can facilitate the modulation of the sampled evoked biological signal according to HACS.

Also discussed above in detail with block 908 of FIG. 9, in some embodiments, modulating the sampled evoked biological signal further includes converting the carrier sequence code to binary format and modulating the sampled evoked biological signal with the carrier sequence code in binary format. Additionally, in embodiments where the sampled evoked biological signal is sampled and held, modulating the sampled evoked biological signal can include multiplying the sampled evoked biological signal with the carrier sequence code using a logical XOR gate. (See FIGS. 7 and 8).

Referring again to FIG. 14, at block 1416, the method 1400 includes demodulating the modulated evoked biological signal by calculating a convolution of the modulated evoked biological signal with the carrier sequence code resulting in an evoked biological signal spectrum. The evoked biological signal spectrum has a peak to sideband ratio as a function of the carrier sequence code. In other embodiments, the evoked biological signal spectrum represents the evoked biological signal with amplitude increased by a factor proportional to the peak to sideband ratio. As discussed above in detail with block 910 of FIG. 9, in some embodiments, the demodulator 126 can calculate a convolution with the original Barker code used for modulation.

In examples where the sampled evoked biological signal is modulated using a carrier sequence code in binary format, demodulating the modulated evoked biological signal further includes demodulating the modulated evoked biological signal by calculating the convolution of the modulated evoked biological signal with the carrier sequence code in binary format using a logical AND gate. For example, FIG. 3A illustrates exemplary biological signal convolution using HACS and a logical AND gate.

Referring again to FIG. 14, at block 1418 the method 1400 includes calculating deviations between each element of the sampled evoked biological signal and the peak to sideband ratio. As described in detail with block 912 of FIG.

9, in one embodiment, the filter 128 can calculate deviations between the sampled evoked biological signal and the peak to sideband ratio.

At block 1420, the method 1400 includes filtering noise artifacts from the sampled evoked biological signal based on the deviations. As described in detail with block 914 of FIG. 9, in one embodiment, the filter 128 can filter noise artifacts from the sampled evoked biological signal based on the deviations, and output a true evoked biological signal based on the filtering. It is understood that calculating deviations and filtering noise artifacts can be implemented with the method 1400 using the functions and components described above in detail with FIG. 10. Further, at block 1422, the method 1400 includes outputting a true evoked biological signal based on the filtering. In some embodiments, the filter 128 outputs the true evoked biological signal based on the filtering performed at block 1418.

Figure 15:
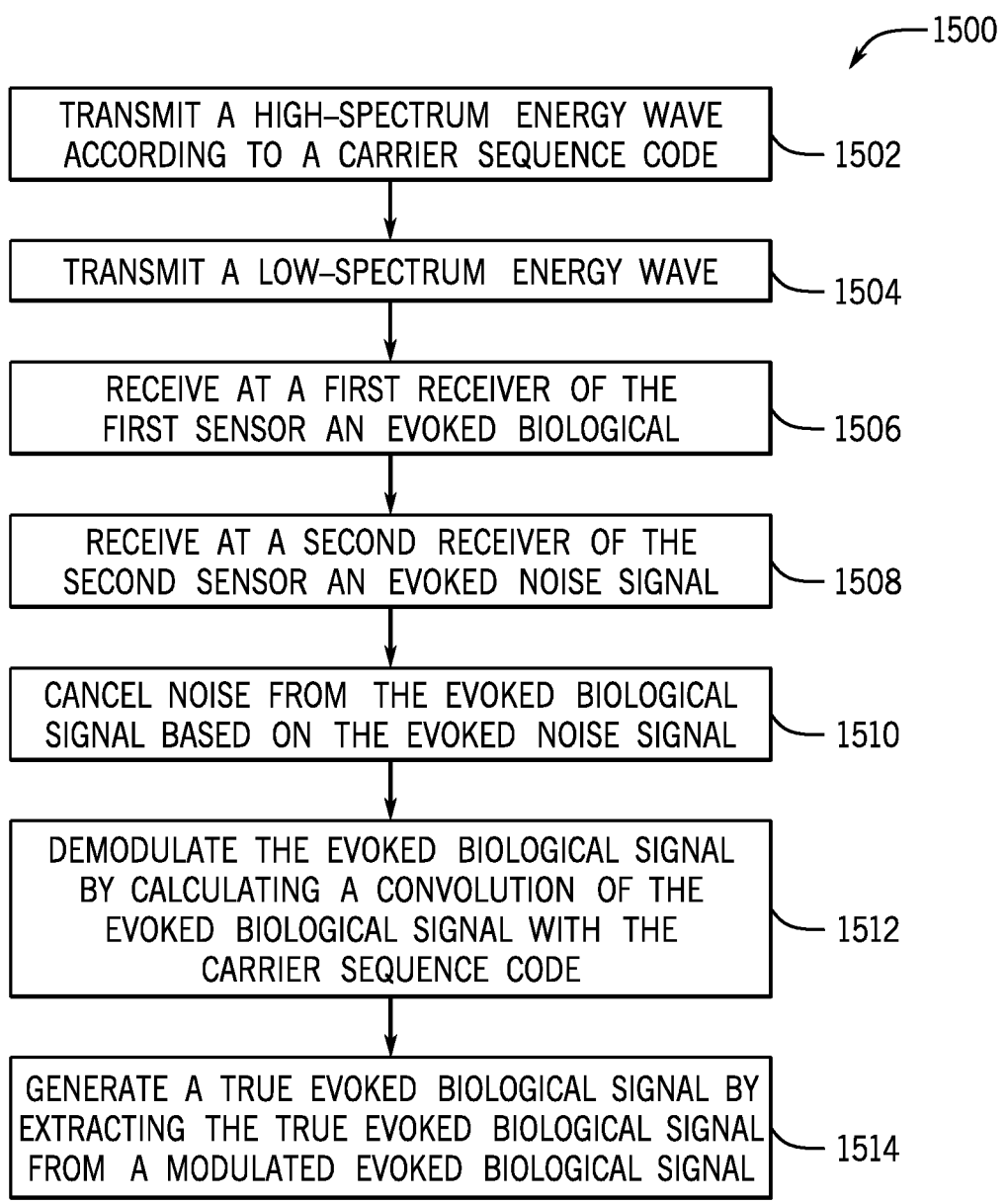
FIG. 15 is a flow diagram of another exemplary method for biological signal processing using highly auto-correlated carrier sequence codes (HACS) according to another exemplary embodiment.

Referring now to FIG. 15, an exemplary method 1500 according to another embodiment for biological signal recording using highly auto-correlated carrier sequence codes (HACS) will be described. In particular, the method 1500 includes noise cancellation using low-spectrum (e.g., blue light) technology. It is understood that in some embodiments, one or more of the blocks in FIG. 15 can be incorporated with one or more of the blocks in FIG. 11. Some of the blocks in FIG. 15 are explained in detail with FIG. 11. At block 1502, the method 1500 includes transmitting a high-spectrum energy wave towards a subject from a first sensor according to a first control signal. In some embodiments, the first control signal represents a carrier sequence code. As discussed above with FIG. 12, the first sensor 104 including the first transmitter 108 transmits first control signals according to a carrier sequence code to the first transmission source 110. Thus, the first transmission source 110 transmits high-spectrum energy (e.g., the IR energy wave 120) towards the subject 106 according to the carrier sequence code. As discussed above in detail with block 1102 of FIG. 11, transmitting the first control signals from the first transmitter 108 of the first sensor 104 to the first transmission source 110 includes the first control signals driving the execution and/or command (e.g., ON/OFF, blinking) of the first transmission source 110 according to the carrier sequence code.

In one embodiment, the high-spectrum energy emitted from the first transmission source 110 is within a red color spectrum. For example, the first transmission source 110 produces energy toward the subject 106 with a wavelength within the red or infrared (IR) emission spectrum. Accordingly, in this embodiment, the first transmission source 110 emits a signal corresponding to a red light (e.g., about 660 nm wavelength) or IR light (e.g., about 780-940 nm wavelength).

At block 1504, the method 1500 includes transmitting a low-spectrum energy wave towards the subject from a second sensor according to a second control signal. In FIG. 12, the second sensor 132 includes the second transmitter 134 to transmit second control signals to the second transmission source 136. Thus, the second transmission source 136 transmits low-spectrum energy (e.g., the blue energy wave 140) towards the subject 106. In some embodiments, the low-spectrum energy is transmitted towards the subject 106 from the second sensor 132 as a continuous energy wave (e.g., not pulsed, not blinked) according to the second control signal. Thus, in one embodiment, the high-spectrum energy is transmitted as pulsed energy and the low-spectrum energy is transmitted as continuous energy.

In one embodiment, the low-spectrum energy transmitted from the second transmission source 136 is within a blue color spectrum. Thus, the second transmission source 136 produces energy toward the subject 106 with a wavelength within the blue emission spectrum. For example, in some embodiments, the second transmission source 136 emits a signal corresponding to a blue light having a wavelength of about 420-495 nm. Based on the above, the second transmission source 136 produces energy in an emission spectrum that is different than the emission spectrum of the energy produced by the first transmission source 110. In particular, the second transmission source 136 produces non-red light energy having low-spectrum energy.

At block 1506, the method 1500 includes receiving at a first receiver of the first sensor an evoked biological signal in response to energy reflection returned from the subject, wherein the evoked biological signal is an analog signal and modulated according to the carrier sequence code. The first sensor 104 also includes the first receiver 106 to receive the evoked biological signal 122 in response to energy reflection returned from the subject 106. In some embodiments, the evoked biological signal 122 is an analog signal and modulated according to the carrier sequence code.

At block 1508, the method 1500 includes receiving at a second receiver of the second sensor an evoked noise signal in response to energy reflection returned from the subject. More specifically, the second sensor 132 also includes the second receiver 138 to receive the evoked noise signal 142 in response to energy reflection returned from the subject 106.

At block 1510, the method 1500 includes cancelling noise from the evoked biological signal 122 based on the evoked noise signal 142. In some embodiments, the filter 128, which is communicatively coupled to the first sensor 102 and the second sensor 132, can cancel noise from the evoked biological signal 122 based on the evoked noise signal 142. In some embodiments, cancelling noise from the evoked biological signal 122 based on the evoked noise signal 142 includes filtering the evoked biological signal 122 with the evoked noise signal 142 using signal cancellation. Thus, as described above in detail with FIGS. 13A and 13B, the signal cancellation of common mode is used to remove noise artifacts from the evoked biological signal 122. More specifically, the output current (Iout) is equal to (Idr−Idf) and can be expressed mathematically as shown in equation (2) above.

At block 1512, the method 1500 includes demodulating the evoked biological signal 122 by calculating a convolution of the evoked biological signal 122 with the carrier sequence code resulting in an evoked biological signal spectrum. The evoked biological signal spectrum has a signal-to-noise ratio proportional to a peak to sideband ratio. In some embodiments, the peak to sideband ratio is a function of the carrier sequence code. As discussed above in detail with FIG. 11 at block 1106, the demodulation is performed by convolving the modulated biological signal with the concatenation of two carrier sequence codes. In a further embodiment, demodulating the modulated evoked biological signal further includes demodulating the modulated evoked biological signal by calculating the convolution of the modulated evoked biological signal with a two's complement of the carrier sequence code in binary format using a logical XOR gate. (See FIG. 7).

Referring again to FIG. 15, at block 1514 the method 1500 includes generating a true evoked biological signal by extracting the true evoked biological signal from the evoked biological signal 122 based on the peak to sideband ratio. In some embodiments discussed above, extracting the true evoked biological signal can include calculating deviations between each element of the sampled evoked biological signal and the peak to sideband ratio. For example, the filter 128 can calculate deviations between the sampled evoked biological signal and the peak to sideband ratio. The filter 128 can filter noise artifacts from the sampled evoked biological signal based on the deviations, and output a true evoked biological signal based on the filtering.

The embodiments discussed herein may also be described and implemented in the context of non-transitory computer-readable medium storing computer-executable instructions, as discussed above. Further, it will be appreciated that various implementations of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A computer-implemented method, comprising:
    transmitting a high-spectrum energy wave towards a subject from a first sensor according to a first control signal;
    transmitting a low-spectrum energy wave towards the subject from a second sensor according to a second control signal;
    in response to transmitting the high-spectrum energy wave and transmitting the low-spectrum energy wave, receiving at a first receiver of the first sensor, an evoked biological signal from the subject and receiving at a second receiver of the second sensor, an evoked noise signal from the subject;
    cancelling noise from the evoked biological signal based on the evoked noise signal;
    calculating a sampled evoked biological signal by sampling the evoked biological signal at a predetermined sampling rate;
    modulating the sampled evoked biological signal with a carrier sequence code resulting in a modulated evoked biological signal, the carrier sequence code having an autocorrelation function;
    demodulating the modulated evoked biological signal by calculating a convolution of the modulated evoked biological signal with the carrier sequence code resulting in an evoked biological signal spectrum, the evoked biological signal spectrum having a peak to sideband ratio as a function of the carrier sequence code;
    calculating deviations between each element of the sampled evoked biological signal and the peak to sideband ratio;
    filtering noise artifacts from the sampled evoked biological signal based on the deviations; and
    outputting a true evoked biological signal based on the filtering.

2. The computer-implemented method of claim 1, wherein modulating the sampled evoked biological signal further includes converting the carrier sequence code to binary format and modulating the sampled evoked biological signal with the carrier sequence code in binary format.

3. The computer-implemented method of claim 2, wherein demodulating the modulated evoked biological signal further includes demodulating the modulated evoked biological signal by calculating the convolution of the modulated evoked biological signal with the carrier sequence code in binary format using a logical AND gate.

4. The computer-implemented method of claim 1, wherein transmitting the high-spectrum energy wave towards the subject from the first sensor according to the first control signal includes, transmitting the high-spectrum energy wave towards the subject from the first sensor as a pulsed energy wave according to the first control signal.

5. The computer-implemented method of claim 1, wherein transmitting the low-spectrum energy wave towards the subject from the second sensor according to the second control signal includes, transmitting the low-spectrum energy wave towards the subject from the second sensor as a continuous energy wave according to the second control signal.

6. The computer-implemented method of claim 1, wherein filtering noise artifacts from the sampled evoked biological signal based on the deviations further includes, comparing the deviation of each element of the sampled evoked biological to a predetermined threshold and filtering respective elements of the sampled evoked biological signal based on the comparison.

7. The computer-implemented method of claim 1, wherein cancelling noise from the evoked biological signal based on the evoked noise signal includes, filtering the evoked biological signal with the evoked noise signal using signal cancellation.

8. The computer-implemented method of claim 1, wherein the evoked biological signal spectrum represents the evoked biological signal with amplitude increased by a factor proportional to the peak to sideband ratio.

9. A computer-implemented method, comprising:
    transmitting a high-spectrum energy wave towards a subject from a first sensor according to a first control signal, wherein the first control signal represents a carrier sequence code;
    transmitting a low-spectrum energy wave towards the subject from a second sensor according to a second control signal;
    receiving at a first receiver of the first sensor an evoked biological signal in response to energy reflection returned from the subject, wherein the evoked biological signal is an analog signal and modulated according to the carrier sequence code;
    receiving at a second receiver of the second sensor an evoked noise signal in response to energy reflection returned from the subject;
    cancelling noise from the evoked biological signal based on the evoked noise signal;
    demodulating the evoked biological signal by calculating a convolution of the evoked biological signal with the carrier sequence code resulting in an evoked biological signal spectrum, the evoked biological signal spectrum having signal-to-noise ratio proportional to a peak to sideband ratio, wherein the peak to sideband ratio is a function of the carrier sequence code; and
    generating a true evoked biological signal by extracting the true evoked biological signal from the evoked biological signal based on the peak to sideband ratio.

10. The computer-implemented method of claim 9, wherein transmitting the low-spectrum energy wave towards the subject from the second sensor according to the second control signal includes, transmitting the low-spectrum energy wave towards the subject from the second sensor as a continuous energy wave according to the second control signal.

11. The computer-implemented method of claim 9, wherein the carrier sequence code has an auto correlation function.

12. The computer-implemented method of claim 9, wherein the carrier sequence code is a concatenation of two carrier sequences codes each having a different length.

13. A system, comprising:
a first sensor including a first transmitter to transmit first control signals to a first transmission source, wherein the first transmission source transmits a high-spectrum energy wave towards a subject according to the first control signals, the first sensor further including a first receiver to receive an evoked biological signal in response to energy reflection returned from the subject, wherein the evoked biological signal is an analog signal;
a second sensor, communicatively coupled to the first sensor, the second sensor including a second transmitter to transmit second control signals to a second transmission source, wherein the second transmission source transmits a low-spectrum energy wave towards the subject according to the second control signals, the second sensor further including a second receiver to receive an evoked noise signal in response to energy reflection returned from the subject;
a filter, communicatively coupled to the first sensor and the second sensor, wherein the filter cancels noise from the evoked biological signal based on the evoked noise signal;
a system clock, communicatively coupled to the first sensor, the second sensor, and the filter, to generate a sampled evoked biological signal at a predetermined sampling rate;
a modulator, communicatively coupled to the first sensor, the second sensor, and the filter, to receive the sampled evoked biological signal and modulate the sampled evoked biological signal with a carrier sequence code having an autocorrelation function; and
a demodulator, communicatively coupled to the first sensor, the second sensor, and the filter, to receive the modulated evoked biological signal and demodulate the modulated evoked biological signal by calculating a convolution of the modulated evoked biological signal with the carrier sequence code resulting in an evoked biological signal spectrum, the evoked biological signal spectrum having a peak to sideband ratio as a function of the carrier sequence code;
wherein the filter calculates deviations between the sampled evoked biological signal and the peak to sideband ratio, filters noise artifacts from the sampled evoked biological signal based on the deviations, and outputs a true evoked biological signal based on the filtering.

14. The system of claim 13, wherein the high-spectrum energy wave is within a red color spectrum and the low-spectrum energy wave is within a blue color spectrum.

15. The system of claim 13, wherein the filter removes elements of the sampled evoked biological signal if the respective deviation meets a predetermined threshold outside of the peak to sideband ratio.

16. A system, comprising:
a first sensor including a first transmitter to transmit first control signals according to a carrier sequence code to a first transmission source, wherein the first transmission source transmits high-spectrum energy towards a subject according to the carrier sequence code, the carrier sequence code having an autocorrelation function,
wherein the first sensor further includes a first receiver to receive an evoked biological signal in response to energy reflection returned from the subject, wherein the evoked biological signal is an analog signal and modulated according to the carrier sequence code;
a second sensor including a second transmitter to transmit second control signals to a second transmission source, wherein the second transmission source transmits low-spectrum energy towards the subject,
wherein the second sensor further includes a second receiver to receive an evoked noise signal in response to energy reflection returned from the subject;
a filter including an amplifier for cancelling noise from the evoked biological signal based on the evoked noise signal;
a demodulator to demodulate the evoked biological signal by calculating a convolution of the evoked biological signal with the carrier sequence code resulting in an evoked biological signal spectrum, the evoked biological signal spectrum having signal-to-noise ratio proportional to a peak to sideband ratio, wherein the peak to sideband ratio is a function of the carrier sequence code,
wherein the demodulator generates a true evoked biological signal by extracting the true evoked biological signal from the evoked biological signal based on the peak to sideband ratio.

17. The system of claim 16, wherein the carrier sequence code is a concatenation of two carrier sequences codes each having a different length.

18. The system of claim 16, wherein the demodulator further demodulates the evoked biological signal by calculating the convolution of the evoked biological signal with a two's complement of the carrier sequence code in binary format using a logical XOR gate.

19. The system of claim 16, wherein the second transmission source transmits low-spectrum energy towards the subject as a continuous energy wave.

20. The system of claim 19, wherein the low-spectrum energy has a wavelength corresponding to visible blue light.

* * * * *